United States Patent
Gregory

(10) Patent No.: US 9,994,813 B2
(45) Date of Patent: Jun. 12, 2018

(54) ROLE FOR THE PERLMAN SYNDROME EXONUCLEASE DIS3L2 IN THE LIN28-LET-7 PATHWAY

(71) Applicant: Children's Medical Center Corporation, Boston, MA (US)

(72) Inventor: Richard I. Gregory, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days. days.

(21) Appl. No.: 14/776,700

(22) PCT Filed: Mar. 14, 2014

(86) PCT No.: PCT/US2014/028580
§ 371 (c)(1),
(2) Date: Sep. 14, 2015

(87) PCT Pub. No.: WO2014/144251
PCT Pub. Date: Sep. 18, 2014

(65) Prior Publication Data
US 2016/0032242 A1    Feb. 4, 2016

Related U.S. Application Data

(60) Provisional application No. 61/799,481, filed on Mar. 15, 2013.

(51) Int. Cl.
*C12N 5/0735* (2010.01)
*C12N 15/113* (2010.01)
*C12N 5/074* (2010.01)

(52) U.S. Cl.
CPC ......... *C12N 5/0606* (2013.01); *C12N 5/0607* (2013.01); *C12N 15/113* (2013.01); *C12N 2310/14* (2013.01); *C12N 2310/141* (2013.01); *C12N 2501/40* (2013.01)

(58) Field of Classification Search
CPC .................................................. C12N 5/0606
See application file for complete search history.

(56) References Cited

FOREIGN PATENT DOCUMENTS

WO    WO 2012/135081 A2    10/2012

OTHER PUBLICATIONS

Piskounva et al. (2008, JBC, vol. 283(31), pp. 21310-21314).*
Brevini et al., 2010, Theriogenology, vol. 74, pp. 544-550.*
Paris et al. (2010, Theriogenology, vol. 74, pp. 516-524).*
Munoz et al. (2008, Theriogenology, vol. 69, pp. 1159-1164).*
Gomez et al. (2010, Theriogenology, vol. 74, pp. 498-515).*
Jean et al. (2013, Develop. Growth Differ., vol. 55, pp. 41-51).*
Buta et al. (2013, Stem Cell Res., vol. 11, pp. 552-562).*
Astuti et al. "Germline mutations in DIS3L2 cause the Perlman syndrome of overgrowth and Wilms tumor susceptibility" Nat. Genet. 44(3): 277-84 (Feb. 5, 2012).
Chang et al. "A role for the Perlman syndrome exonuclease Dis3L2 in the Lin28-let-7 pathway" Nature 497 (7448) 244-8 (May 9, 2013).
Thornton et al. Lin28-mediated control of let-7 microRNA expression by alternative TUTases Zcchc11 (TUT4) and Zcchc6 (TUT7) RNA 18(10) 1875-85 (Aug. 16, 2012).
Ustianenko et al. "Mammalian DIS3L2 exoribonuclease targets the uridylated precursors of let-7 mIRNAs" RNA 19(12): 1632-8 (Oct. 18, 2013).
Chang et al., Trim71 cooperates with microRNAs to repress Cdkn1a expression and promote embryonic stem cell proliferation. Nat Commun. Jun. 26, 2012;3:923. doi: 10.1038/ncomms1909.
Chang et al., "Lin-28B transactivation is necessary for Myc-mediated let-7 repression and proliferation," Pro. Natl. Acad. Sci. USA 106, 3384-3389, 2009.
Dangi-Garimella et al., "Raf kinase inhibitory protein suppresses a metastasis signaling cascade involving LIN28 and let-7," EMBO J. 28, 347-358, 2009.
Diskin et al., "Common variation at 6q16 within HACE1 and LIN28B influences susceptibility to neuroblastoma," Nat. Genet. 44, 1126-1130, 2012.
Ebert et al., "Roles for microRNAs in conferring robustness to biological processes," Cell 149, 515-524, 2012.
Fabian et al., "Regulation of mRNA translation and stability by microRNAs," Annu. Rev. Biochem. 79, 351-379, 2010.
Hagan et al., "Lin28 recruits the TUTase Zcchc11 to inhibit let-7 maturation in mouse embryonic stem cells," Nat. Struct. Mol. Biol. 16, 1021-1025, 2009.
Heo et al., "Lin28 mediates the terminal uridylation of let-7 precursor MicroRNA," Mol. Cell 32, 276-284, 2008.
Heo et al., "TUT4 in concert with Lin28 suppresses microRNA biogenesis through pre-microRNA uridylation," Cell 138, 696-708, 2009.
Iliopoulos et al., "An epigenetic switch involving NF-kappaB, Lin28, Let-7 MicroRNA, and IL6 links inflammation to cell transformation," Cell 139, 693-706, 2009.
Iorio et al., "MicroRNA dysregulation in cancer: diagnostics, monitoring and therapeutics. A comprehensive review," EMBO Mol. Med. 4, 143-159, 2012.
Melton et al., "Opposing microRNA families regulate self-renewal in mouse embryonic stem cells," Nature 463, 621-626, 2010. Author manuscript.
Mendell et al., "MicroRNAs in stress signaling and human disease," Cell 148, 1172-1187, 2012. Author manuscript.

(Continued)

Primary Examiner — Thaian N Ton
Assistant Examiner — David A. Montanari
(74) Attorney, Agent, or Firm — Wolf, Greenfield & Sacks, P.C.

(57) ABSTRACT

The 3'-5' exonuclease, Dis3l2, is responsible for the decay of uridylated pre-let-7 miRNA. Biochemical reconstitution assays revealed that 3' oligouridylation stimulates Dis3l2 activity in vitro, and knockdown of Dis3l2 in mouse embryonic stem cells leads to the stabilization of pre-let-7 miRNA. These Dis3l2-depleted stem cells displayed elevated expression of pluripotency genes and delayed differentiation. The present disclosure establishes 3' oligouridylation as an RNA decay signal for Dis3l2 and identifies the first physiological RNA substrate of this exonuclease.

9 Claims, 25 Drawing Sheets

(56) References Cited

OTHER PUBLICATIONS

Mandol et al., "Let's make it happen: the role of let-7 microRNA in development," Curr. Top. Dev. Biol. 99, 1-30, 2012.

Nam et al., "Molecular Basis for Interaction of let-7 MicroRNAs with Lin28," Cell 147, 1080-1091, 2011.

Newman et al., "Lin-28 interaction with the Let-7 precursor loop mediates regulated microRNA processing," RNA 14, 1539-1549, 2008.

Norbury, "3' Uridylation and the regulation of RNA function in the cytoplasm," Biochem. Soc. Trans. 38, 1150-1153, 2010.

Pasquinelli et al., "Conservation of the sequence and temporal expression of let-7 heterochronic regulatory RNA," Nature 408, 86-89, 2000.

Piskounova et al., "Oncogenic Lin28A and Lin28B Inhibit let-7 MicroRNA Biogenesis by Distinct Mechanisms," Cell 147, 1066-1079, 2011. Author manuscript.

Reinhart et al., "The 21-nucleotide let-7 RNA regulates developmental timing in Caenorhabditis elegans," Nature 403, 901-906, 2000.

Rissland et al., "Decapping is preceded by 3' uridylation in a novel pathway of bulk mRNA turnover," Nat. Struct. Mol. Biol. 16, 616-623, 2009. Author manuscript.

Rough et al., "The let-7 family of microRNAs," Trends Cell bBiol. 18, 505-516, 2008.

Rybak et al., "A feedback loop comprising lin-28 and let-7 controls pre-let-7 maturation during neural stem-cell commitment," Nat. Cell Biol. 10, 987-993, 2008.

Schmidt et al., "The human cytoplasmic RNA terminal U-transferase ZCCHC11 targets histone mRNAs for degradation," RNA 17, 29-44, 2011.

Siomi et al., "Posttranscriptional regulation of microRNA biogenesis in animals," Mol. Cell 38, 323-332, 2010.

Staals et al., "Dis3-like 1: a novel exoribonuclease associated with the human exosome," EMBO J. 29, 2358-2367, 2010.

Thornton et al., "How does Lin28 let-7 control development and disease?" Trends Cell Biol. 22, 474-482, 2012. Author manuscript.

Tomecki et al., "The human core exosome interacts with differentially localized processive RNases: hDIS3 and hDIS3L," EMBO J. 29, 2342-2357, 2010.

Viswanathan et al., "Lin28: A microRNA regulator with a macro role," Cell 140, 445-449, 2010.

Viswanathan et al., "Selective blockade of microRNA processing by Lin28," Science 320, 97-100, 2008. Author manuscript.

Viswanathan et al., "Lin28 promotes transformation and is associated with advanced human malignancies," Nat. Genet. 41, 843-848, 2009.

Yu et al., "Induced pluripotent stem cell lines derived from human somatic cells," Science 318, 1917-1920, 2007.

Zhang et al., "Glycine decarboxylase activity drives non-small cell lung cancer tumor-initiating cells and tumorigenesis," Cell 148, 259-272, 2012.

\* cited by examiner

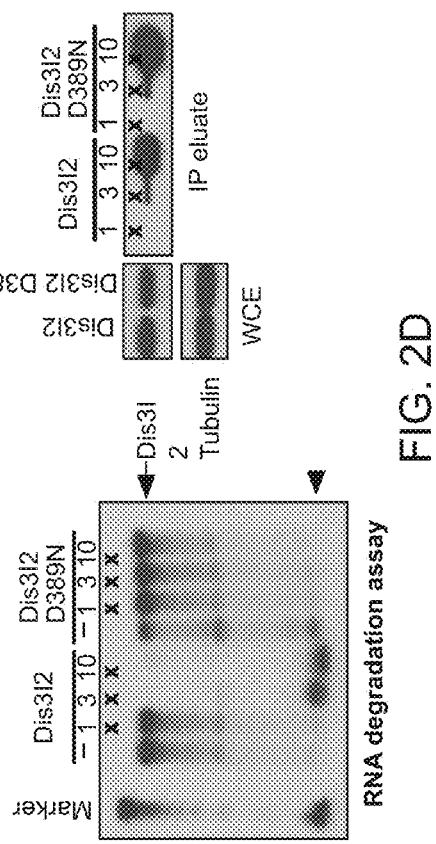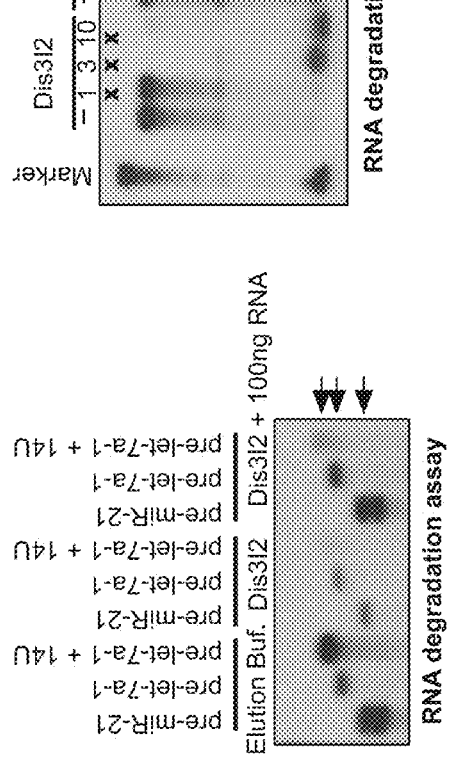

|  | Half-life (min.) |
|---|---|
| pre-let-7a-1 | 68.04 |
| pre-let-7a-1 + 14U | 6.35 |

RNA degradation assay pre-let-7g Northern blot

U6

RNA degradation assay

RNA degradation assay

Western Blot

FIG. 9C-1 pri-let-7a-1 PCR product blast:

```
Query    1      GAGACCCCATGAATGCAGACTTTTCCATCACCCTTAGGAAAGACAGTAGATTGTATAGTTA    60
                ||||||||||||||||||||||||||||||||||||||||||||||||||||||||||||
Sbjct    8790586 GAGACCCCATGAATGCAGACTTTTCCATCACCCTTAGGAAAGACAGTAGATTGTATAGTTA  8790645

Query    61     TCTCCCAGTGGTGGGTGTGACCCTAAAACTATACAACCTACTACCTCATCCCACAGTGAA   120
                ||||||||||||||||||||||||||||||||||||||||||||||||||||||||||||
Sbjct    8790646 TCTCCCAGTGGTGGGTGTGACCCTAAAACTATACAACCTACTACCTCATCCCACAGTGAA  8790705

Query    121    GAGAACATCCAGGGTGAATGTTGAAAG   147
                |||||||||||||||||||||||||||
Sbjct    8790706 GAGAACATCCAGGGTGAATGTTGAAAG  8790732
``` pre-let-7a-1 PCR product blast:

```
Query    1      GGAAAGACAGTAGATTGTATAGTTATCTCCCAGTGGTGGGTGTGACCCTAAAACTATACA    60
                ||||||||||||||||||||||||||||||||||||||||||||||||||||||||||||
Sbjct    85     GGAAAGACAGTAGATTGTATAGTTATCTCCCAGTGGTGGGTGTGACCCTAAAACTATACA    26

Query    61     ACCTACTACCTCA    73
                |||||||||||||
Sbjct    25     ACCTACTACCTCA    13
```

FIG. 9C-2 pri-let-7g PCR product blast:

```
Query     1 GTTCTCTTTTGCCTGATTCCAGGCTGAGGTAGTAGTTTGTACAGTTTGAGGGTCTATGAT    60
            ||||||||||||||||||||||||||||||||||||||||||||||||||||||||||||
Sbjct 5086769 GTTCTCTTTTGCCTGATTCCAGGCTGAGGTAGTAGTTTGTACAGTTTGAGGGTCTATGAT 5086828

Query    61 ACCACCCGGTACAGGAGATAACTGTACAGGCCACTGCCTTGCCAGGAACAGTGCACCAGC   120
            ||||||||||||||||||||||||||||||||||||||||||||||||||||||||||||
Sbjct 5086829 ACCACCCGGTACAGGAGATAACTGTACAGGCCACTGCCTTGCCAGGAACAGTGCACCAGC 5086888

Query   121 TACCAAATG   129
            |||||||||
Sbjct 5086889 TACCAAATG   5086897
``` pre-let-7g PCR product blast:

```
Query     1 TGAGGTAGTAGTTTGTACAGTTTGAGGGTCTATGATACCACCCGGTACAGGAGATAACTG    60
            ||||||||||||||||||||||||||||||||||||||||||||||||||||||||||||
Sbjct     7 TGAGGTAGTAGTTTGTACAGTTTGAGGGTCTATGATACCACCCGGTACAGGAGATAACTG    66

Query    61 TACAGGCCACTGCCTTGC    78
            ||||||||||||||||||
Sbjct    67 TACAGGCCACTGCCTTGC    84
```

FIG. 9C-3

U6 PCR product blast:

```
Query   1     CTCGCTTCGGCAGCACATATACTAAAAATTGGAACGATATACAGAGAAGATTAGCATGGCCCC   60
              ||||||||||||||||||||||||||||||||||||||||||||||||||||||||||||||
Sbjct   4     CTCGCTTCGGCAGCACATATACTAAAAATTGGAACGATATACAGAGAAGATTAGCATGGCCCC   63

Query   61    TGCGCAAGGATGACACGCAAATTCGTGAAGCGTT   94
              ||||||||||||||||||||||||||||||||||
Sbjct   64    TGCGCAAGGATGACACGCAAATTCGTGAAGCGTT   97
```

ACTB PCR product blast:

```
Query   1     CAGAAGGAGATTACTGCTCTGGCTCCTAGCACCATGAAGATCAAGATCATTGCTCCTCCT   60
              ||||||||||||||||||||||||||||||||||||||||||||||||||||||||||||
Sbjct   1019  CAGAAGGAGATTACTGCTCTGGCTCCTAGCACCATGAAGATCAAGATCATTGCTCCTCCT   1078

Query   61    GAGCGCAAGTACTCTGTGTGGATCGGTGGCTCCATCCTGGCCTCCACTGTCCACCTTCCAG   120
              ||||||||||||||||||||||||||||||||||||||||||||||||||||||||||||
Sbjct   1079  GAGCGCAAGTACTCTGTGTGGATCGGTGGCTCCATCCTGGCCTCCACTGTCCACCTTCCAG   1138

Query   121   CAGATGTGGATCAGCAAGCAGGAGTA   146
              ||||||||||||||||||||||||||
Sbjct   1139  CAGATGTGGATCAGCAAGCAGGAGTA   1164
```

ROLE FOR THE PERLMAN SYNDROME EXONUCLEASE DIS3L2 IN THE LIN28-LET-7 PATHWAY

RELATED APPLICATIONS

This application is a national stage filing under 35 U.S.C. § 371 of international application number PCT/US2014/028580, filed Mar. 14, 2014, which was published under PCT Article 21(2) in English and claims the benefit under 35 U.S.C. § 119(e) of U.S. provisional application No. 61/799,481, filed Mar. 15, 2013, each of which is incorporated herein by reference in its entirety.

GOVERNMENT FUNDING

This invention was made with government support under Grant Number R01GM086386 awarded by the National Institutes of Health. The government has certain rights in the invention.

BACKGROUND

The pluripotency factor Lin28 blocks the expression of let-7 microRNAs in undifferentiated cells during development and functions as an oncogene in a subset of cancers. Lin28 binds to let-7 precursor RNAs and recruits 3' terminal uridylyl transferases (TUTases) to selectively inhibit let-7 biogenesis. Uridylated pre-let-7 is refractory to processing by Dicer and is rapidly degraded by an unknown ribonuclease.

SUMMARY

As described herein, the 3'-5' exonuclease, Dis3l2, is responsible for the decay of uridylated pre-let-7 miRNA. Biochemical reconstitution assays revealed that 3' oligouridylation stimulates Dis3l2 activity in vitro, and knockdown of Dis3l2 in mouse embryonic stem cells leads to the stabilization of pre-let-7 miRNA. These Dis3l2-depleted stem cells displayed elevated expression of pluripotency genes and delayed differentiation. The present disclosure establishes 3' oligouridylation as an RNA decay signal for Dis3l2 and identifies the first physiological RNA substrate of this exonuclease, which is mutated in the Perlman syndrome of fetal overgrowth and predisposition to Wilms' tumor.

Thus, various aspects and embodiments of the present disclosure relate to methods of expanding a pool of pluripotent stem cells (e.g., human pluripotent stem cells), the methods comprising contacting pluripotent stem cells with an effective amount of at least one agent that inhibits Dis3l2 to prevent differentiation of at least a portion of the pluripotent stem cells.

In some embodiments, a level of 3' uridylated pre-let-7 microRNA transcript obtained from the pool of pluripotent stem cells (e.g., human pluripotent stem cells) is increased as compared to a control level of 3' uridylated pre-let-7 microRNA transcript.

In some embodiments, a method is performed in vitro.

In some embodiments, levels of expression of Sox2, Nanog and/or Oct are increased in a pool of pluripotent stem cells (e.g., human pluripotent stem cells) as compared to control levels of expression of Sox2, Nanog and/or Oct, respectively.

In some embodiments, pluripotent stem cells (e.g., human pluripotent stem cells) display increased rates of proliferation as compared to control rates of proliferation.

In some embodiments, at least one agent inhibits Dis3l2 and that at least one agent inhibits gene expression of Dis3l2. In some embodiments, the at least one agent that inhibits gene expression of Dis3l2 is an RNA interference (RNAi) molecule. In some embodiments, the RNAi molecule is a short hairpin RNA (shRNA) or a short interfering RNA (siRNA).

In some embodiments, the inhibitor of Dis3l2 is an antisense nucleic acid.

In some embodiments, the at least one agent that inhibits Dis3l2 is an agent that inhibits Dis3l2 exonuclease activity.

Various other aspects and embodiments of the present disclosure relate to methods of promoting degradation of uridylated RNA, the methods comprising contacting an RNA with an effective amount of Dis3l2 to promote degradation of uridylated RNA.

In some embodiments, a uridylated RNA is 3' uridylated pre-let 7 microRNA.

In some embodiments, a method is carried out in vitro.

In yet other aspects and embodiments, provided herein are methods of stabilizing pre-let-7 microRNA in cells, the methods comprising contacting the cells with an effective amount of at least one agent that inhibits Dis3l2 to stabilize pre-let-7 microRNA.

In some embodiments, a level of 3' uridylated pre-let-7 microRNC transcript in the cells is increased as compared to a control level of 3' uridylated pre-let-7 microRNC transcript.

In some embodiments, a method is performed in vitro.

In some embodiments, at least one agent that inhibits Dis3l2 is an agent that inhibits gene expression of Dis3l2. In some embodiments, at least one agent that inhibits gene expression of Dis3l2 is an RNA interference (RNAi) molecule. In some embodiments, a RNAi molecule is a short hairpin RNA (shRNA) or a short interfering RNA (siRNA). In some embodiments, a inhibitor of Dis3l2 is an antisense nucleic acid.

In some embodiments, at least one agent that inhibits Dis3l2 is an agent that inhibits Dis3l2 exonuclease activity.

These and other aspects of the invention are described in more detail herein.

The invention is not limited in its application to the details of construction and the arrangement of components set forth in the following description or illustrated in the drawings. The invention is capable of other embodiments and of being practiced or of being carried out in various ways. Each of the above embodiments and aspects may be linked to any other embodiment or aspect. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The accompanying drawings are not intended to be drawn to scale. For purposes of clarity, not every component may be labeled in every drawing. In the drawings.

DETAILED DESCRIPTION

Figure 1A:
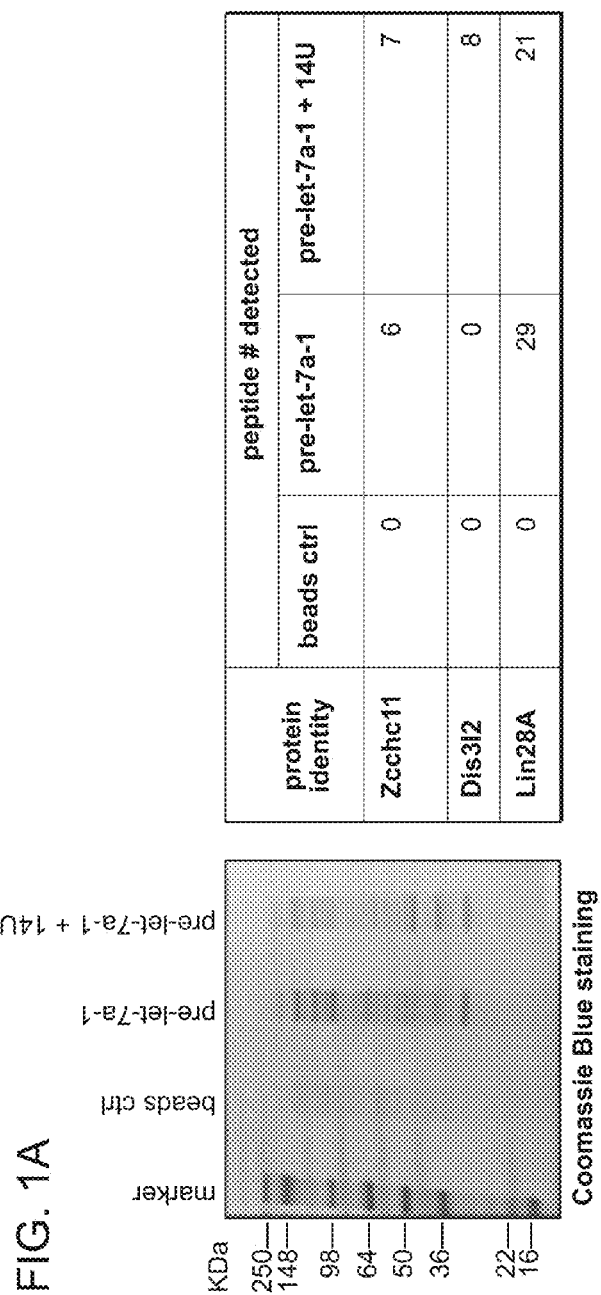
FIG. 1. The Perlman syndrome exonuclease Dis3l2 is associated with uridylated pre-let-7. (a) The affinity-purified proteins were separated on SDS-PAGE (4-20% gradient) followed by Coomassie blue staining, and analyzed by mass spectrometry. The number of individual peptides corresponding to each protein is indicated in the table. (b) Diagrammatic representation of mouse Dis3l2 protein, Protein accession number (NCBI): NP_001165628.1. Cold-shock domains (CSD) are depicted in yellow, RNB—ribonuclease II domain is in red, and the S1 RNA-binding domain is purple. aa, amino acids. Also indicated is the conserved catalytic Aspartic Acid (D) that was mutated to Asparagine (N) to generate a catalytically inactive Dsi3l2 protein (c) Western blotting for Zcchc11, Dis3l2, and Lin28A on the affinity-purified proteins. (d) Dox-induced cell extracts prepared from KH2 ESCs expressing Flag-Lin28A were immunoprecipitated by α-Flag beads. Input and the associated proteins were examined by Western blotting. (e) V6.5 ESC were transfected with FLAG-Lin28A or FLAG-Lin28A W46A expression vectors or empty vector. Cells extracts were prepared in the presence or absence of recombinant RNasin or RNase A. Proteins were immunoprecipitated by α-Flag beads and input and immunoprecipitates were examined by Western blotting using the indicated antibodies.

Posttranscriptional gene regulation by microRNAs (miRNAs) impacts many developmental and physiological processes (Ebert and Sharp, 2012; Mendell and Olson, 2012). Functioning by base-pairing with target messenger RNAs (mRNAs) of complementary sequence, these ~22 nucleotides (nt) RNAs recruit the miRNA-induced silencing complex (miRISC) for translational repression and mRNA deadenylation and decay (Fabian et al., 2010). Of particular relevance is the ancient let-7 family of miRNAs that are essential for normal development of *C. elegans*. Loss of their tumor suppressor function impacts various human cancers in which expression of oncogenic target genes is elevated (Mondol and Pasquinelli, 2012; Pasquinelli et al., 2000; Reinhart et al., 2000; Roush and Slack, 2008).

Let-7 expression is dynamically regulated during development by the paralogous RNA-binding proteins Lin28A and Lin28B (Heo et al., 2008; Newman et al., 2008; Rybak et al., 2008; Siomi and Siomi, 2010; Viswanathan et al., 2008). Lin28 was identified genetically as a regulator of developmental timing in worms, and more recently has been linked with controlling developmental timing and growth of mammals as well as maintaining glucose homeostasis (Ambros and Horvitz, 1984; Thornton and Gregory, 2012; Zhu et al., 2010). Lin28 is a pluripotency factor in embryonic stem cells (ESCs), where its expression helps maintain cells in an undifferentiated, proliferative, and pluripotent state by selectively preventing let-7 expression (Chang et al., 2012).

The Lin28-let-7 pathway is normally silent in adult somatic cells expression of Lin28A or Lin28B is associated with a wide variety or human cancers. (Thornton and Gregory, 2012; Viswanathan and Daley, 2010) Inhibition of this oncogenic pathway inhibits the tumorigenicity of human cancer cells in mouse xenograft assays (Iliopoulos et al., 2009; Piskounova et al., 2011; Viswanathan et al., 2009).

Recent work has provided insight into the mechanisms underlying the Lin28-mediated let-7 regulation and the molecular basis for the selective recognition of let-7 family miRNAs. (Nam et al., 2011). Lin28A functions in the cell cytoplasm where it recruits 3' terminal uridylyl transferases (TUTase), Zcchc11 (TUT4) and Zcchc6 (TUT7), that adds an oligouridine tail to pre-let-7 to inhibit Dicer processing and is thought to serve as a signal for the rapid decay of the uridylated RNA by an unknown nuclease (Hagan et al., 2009; Heo et al., 2008; Heo et al., 2009; Thornton et al., 2012; Piskounova et al., 2011). The nuclease responsible for the regulation of pre-let-7 in mouse ESCs and its characteristics are described herein. Using an RNA-affinity purification strategy, Dis3l2 was initially identified as a candidate nuclease that specifically associates with uridylated pre-let-7. Biochemical reconstitution assays using immunopurified or recombinant Dis3l2 protein revealed that 3' oligouridylation stimulates ribonuclease activity in vitro. Knockdown of Dis3l2 in mouse ESCs led to the accumulation of uridylated pre-let-7. Moreover, Dis3l2 is required for normal ESC differentiation; Dis3l2-deficient cells display persistent expression of pluripotency factors in differentiation conditions. These data establish 3' oligouridylation as an RNA decay signal for Dis3l2 and identify the first physiological RNA substrate of this exonuclease that is mutated in the Perlman syndrome of fetal overgrowth and predisposition to Wilms' tumor (Astuti et al., 2012).

Lin28A/B proteins selectively inhibit the biogenesis of the let-7 family of miRNAs in undifferentiated embryonic cells and in cancer (Thornton and Gregory, 2012). Lin28A functions in the cell cytoplasm, where it recruits a 3' terminal uridylyl transferase (TUTase), Zcchc11 (TUT4) or Zcchc6 (TUT7), which adds an oligouridine tail to pre-let-7 that inhibits Dicer processing and is thought to serve as a signal leading the rapid decay of the uridylated RNA by an unknown nuclease (Hagan et al., 2009; Heo et al., 2008; Heo et al., 2009; Thornton et al., 2012). Here, Dis3l2 is identified as a new component of the Lin28/let-7 pathway and as the downstream nuclease responsible for the decay of uridylated pre-let-7. This identification is based on the following observations: First, Dis3l2 specifically associates with uridylated pre-let-7 and not with control pre-let-7 in RNA affinity-purifications from embryonic stem extracts and is detected as a component of a Lin28A-containing ribonucleoprotein complex isolated from ESCs. Second, Flag-affinity purified Dis3l2 (but not catalytically inactive mutant Dis3l2) complexes display substrate preference for uridylated pre-let-7 in RNA degradation assays in vitro. Third, in vitro reconstitution experiments with recombinant Dis3l2 reveal the sufficiency of this enzyme for the preferential degradation of uridylated pre-let-7. Last, knockdown of Dis3l2 led to the specific accumulation of uridylated pre-let-7 in mouse ESCs. Dis3l2 is required in stem cell pluripotency, as evidenced by the fact that Dis3l2-deficient ESCs display defective differentiation.

Dis3l2 belongs to a family of related 3'-5' exonucleases that include Dis3 and Dis3l1 with similar domain organization to bacterial RNase II (Astuti et al., 2012; Staals et al., 2010; Tomecki et al., 2010). Germline mutations in the Dis3l2 gene were recently found to be responsible for Perlman syndrome, a rare, autosomal recessive, fetal overgrowth syndrome (Astuti et al., 2012). In addition to being large, affected individuals are hypotonic, have organomegally, characteristic facial dysmorphism, renal abnormalities, neurodevelopmental problems, and a dramatically high susceptibility Wilms' tumors (Nephroblastoma) with >60% of surviving children developing (often bilateral) Wilms' tumors. Dis3l2 was found to be mutated in ~30% of sporadic Wilms' tumors analyzed with evidence also for loss of both Dis3l2 alleles (Astuti et al., 2012).

Described herein is the first physiologic RNA substrate of Dis3l2. Considering the similarities between the disease phenotypes associated with Dis3l2 deletion and those caused by Lin28 gain-of-function (overgrowth and tumorigenesis), it is tempting to speculate that this novel role of Dis3l2 in the Lin28-let-7 regulatory pathway is relevant to Perlman syndrome and cancer. Dis3l2 knockdown in ESCs leads to compromised cell differentiation. How exactly Dis3l2-deficiceny contributes to this differentiation defect in ESCs remains an important area for future investigation. Moreover, in light of these data, it will be important to explore the relationship between oncogenic Lin28A and the potential tumor suppressive role of Dis3l2 in Wilms' tumors as well as other Lin28A-expressing tumors.

Identification of a decay pathway for uridylated RNAs raises questions about how widespread this type of regulation might be on a transcriptome scale, as well as the mechanism by which oligouridylation promotes Dis3l2 ribonucleolytic activity. It will be of interest to explore and identify additional RNAs that might be subject to this type of regulation. So far there are few known examples where 3' uridylation can serve as a decay signal; these include histone mRNA regulation during the mammalian cell cycle, as well as the report in *Schizosaccharomyces pombe* of widespread uridylation-dependent mRNA decapping and decay (Mullen and Marzluff, 2008; Norbury, 2010; Rissland and Norbury, 2009; Schmidt et al., 2011). This model has analogies with 3'-5' exonuclease decay in other systems where the addition of homopolymeric nucleotide tracts promote RNA degradation; for example RNA decay in *E. Coli* by the 'Degradosome' is stimulated by poly(A) tails as short as 5-nt (Blum et al., 1999; Carpousis et al., 1999). Similarly in *Saccharomyces cerevisiae* the Trf4/Air2/Mtr4 polyadenylation (TRAMP) complex catalyzes the addition of oligoA-tail that promotes 3'-5' RNA decay by the exosome as part of a nuclear RNA surveillance mechanism (LaCava et al., 2005). Considering these aforementioned examples it seems likely that this type of regulation whereby ribonucleotidyl transferase activity confers substrate specificity for the downstream exonuclease may be much more common than we currently appreciate. In the case of pre-let-7 the 3' oligouridylation has two consequences; 1) to block Dicer processing, and 2) to stimulate decay by Dis3l2, therefore even though Dis3l2 displays relatively modest substrate preference for uridylated pre-let-7 in vitro, the two-step mechanism safeguards against the production of mature let-7 miRNA and helps explain why we did not observe accumulation of mature let-7 in Dis3L2-depleted cells.

microRNAs

The present disclosure is related, in part, to the regulation of pre-let 7 microRNA (miRNA) processing. The let-7 family of miRNAs dynamically regulated during development, and loss of their tumor suppressor function impacts various human cancers in which expression of oncogenic target genes is elevated.

As used herein, "microRNA," "miRNA," and "miR" may be used interchangeably to refer to genomically encoded non-coding RNAs that may regulate gene expression, particularly during development. These endogenous RNA molecules typically act as gene silencers to regulate the expression of protein-coding genes at the post-transcriptional level. Endogenous microRNA are small RNAs naturally present in the genome that are capable of modulating the productive utilization of mRNA. An miRNA is expressed from a much longer RNA-coding gene as a primary transcript known as a pri-miRNA which is processed, in the cell nucleus, to a 70-nucleotide stem-loop structure called a pre-miRNA by a microprocessor complex of an RNase III enzyme, Drosha, and a dsRNA-binding protein, DGCR8. The dsRNA portion of this pre-miRNA is bound and cleaved by Dicer to produce the mature miRNA molecule of about 22 nucleotides. miRNAs are important in development and differentiation, and thus the altered expression of miRNAs may be used to alter development and differentiation during tissue engineering and other applications. As used herein, a "stem-loop structure" refers to a nucleic acid having a secondary structure that includes a region of nucleotides which are known or predicted to form a double strand (stem portion) that is linked on one side by a region of predominantly single-stranded nucleotides (loop portion). The term "hairpin" may be used herein to refer to a stem-loop structure.

As used herein, "pri-miRNA" refers to a precursor microRNA molecule having a microRNA sequence in the context of microRNA flanking sequences. A precursor microRNA, also referred to as large RNA precursors, are composed of any type of nucleic acid based molecule capable of accommodating the microRNA flanking sequences and the microRNA sequence. A precursor microRNA molecule may be processed in vivo or in vitro to produce a mature microRNA (miRNA). A precursor microRNA molecule is processed in a host cell by a ribonuclease enzyme or enzymes. One example of a ribonuclease enzyme that processes precursor microRNA molecules is the RNase II ribonuclease Dicer.

As used herein, "pre-miRNA" refers to the intermediate miRNA species from the processing of a pre-miRNA to a mature miRNA. Pre-miRNAs are produced from the processing of a pri-miRNA in the nucleus into a pre-miRNA. Pre-miRNAs undergo additional processing in the cytoplasm to form mature miRNA. Pre-miRNAs are approximately 70 nucleotides long, but can be less than 70 nucleotides or more than 70 nucleotides.

As an example, pri-let-7 may be processed into pre-let-7, which may be further processed into mature let-7. As used herein, "let-7" refers to the nucleic acid encoding the let-7 miRNA family members, homologues and variants thereof, including conservative substitutions, additions, and deletions therein not adversely affecting the structure or function. In some embodiments, let-7 nucleic acid encodes let-7 from *C. elegans* (NCBI Accession No. AY390762). In some embodiments, let-7 nucleic acid encodes let-7 from humans (e.g., NCBI Accession Nos. AJ421724, AJ421725, AJ421726, AJ421727, AJ421728, AJ421729, AJ421730, AJ421731, AJ421732 and biologically active sequence variants thereof, including alleles, and in vitro-generated derivatives of let-7 that demonstrate let-7 activity).

Inhibitor Agents

Examples of inhibitor agents that may be used in accordance with the present disclosure include, without limitation, nucleic acids (e.g., DNA and/or RNA) and nucleic acid analogues; antibodies, including full-length antibodies and antigen-binding antibody fragments, polyclonal antibodies, monoclonal antibodies, chimeric antibodies, and humanized antibodies; proteins, including peptides, peptide-mimetics and aptamers; and small molecules.

In some embodiments, an agent that inhibits Dis3l2 (e.g., silences Dis3l2 gene expression) may be an RNA interference (RNAi) molecule, such as microRNAi, short interfering RNA (siRNA) and short hairpin RNA (shRNA). In some embodiments, an agent that inhibits Dis3l2 may be an antisense nucleic acid.

As used herein, "gene silencing," refers to post-transcriptional gene silencing, which may be the result of mRNA of a particular gene being degraded or blocked. The RNAi inhibitor agents provide herein may, in some embodiments, decrease the expression level of Dis3l2 mRNA by at least about 5%, about 10%, about 20%, about 30%, about 40%, about 50%, about 55%, about 60%, about 70%, about 75%, about 80%, about 85%, about 90%, about 95%, about 99% or about 100% of the mRNA level found in the cell without the presence of an RNAi inhibitor agent.

As used herein, "RNA interference" is a biological process in which RNA molecules inhibit gene expression, typically by causing the degradation of specific mRNA molecules.

As used herein, "siRNA" is a class of double-stranded RNA molecules, which interferes with the expression of specific genes having a nucleotide sequence complementary to the siRNA. siRNAs typically have a well-defined structure: a short (e.g., 21 base pair) double-stranded RNA (dsRNA) with phosphorylated 5' ends and hydroxylated 3' ends with two overhanging nucleotides. The Dicer enzyme catalyzes production of siRNAs from long dsRNAs and small hairpin RNAs (shRNAs). An siRNA for use in accordance with the present disclosure may be about 15 to about 35 base pairs, or about 20 to about 25 base pairs, in length. In some embodiments, the siRNA may be about 15, 16, 17, 18, 19, 20, 21, 22, 23, 24, 25, 26, 27, 28, 29, 30, 31, 32, 33, 34 or 35 base pairs in length.

As used herein, "shRNA" refers to a sequence of RNA that makes a tight hairpin turn that can be used to silence target gene expression through RNA interference (RNAi). Expression of shRNA in cells may be accomplished by delivery of plasmids or through viral or bacterial vectors. For example, in some embodiments, shRNA targeting Dis3l2 may be delivered to a pool of pluripotent stem cells (e.g., human pluripotent stem cells) by transfecting the cells with a plasmid that contains a nucleic acid encoding the shRNA. In some embodiments, bacterial vectors may be used to obtain shRNA expression in cells. In some embodiments, viral vectors (e.g., adeno-associated viruses (AAVs), adenoviruses, and lentiviruses) may be used to obtain shRNA expression in cells. Due to the ability of shRNA to provide specific, long-lasting, gene silencing, shRNA may be used for gene therapy applications.

As used herein, a "stem-loop structure" refers to a nucleic acid having a secondary structure that includes a region of nucleotides which are known or predicted to form a double strand (stem portion) that is linked on one side by a region of predominantly single-stranded nucleotides (loop portion). The term "hairpin" may be used herein to refer to a stem-loop structure.

Stem Cells

As used herein, a "stem cell" refers to an undifferentiated or partially differentiated cell that has the ability to self-renew and has the developmental potential to differentiate into multiple cell types. A "pluripotent cell" refers to a cell with the developmental potential, under different conditions, to differentiate to cell types characteristic of all three germ cell layers, i.e., endoderm (e.g., gut tissue), mesoderm (including blood, muscle, and vessels), and ectoderm (such as skin and nerve).

As used herein, "expanding a pool of pluripotent stem cells" refers to increasing the number of pluripotent stem cells (e.g., human pluripotent stem cells) is a given population. In some embodiments, a population or "pool" of stem cells is an isolated population (e.g., a population of cells that has been removed from its natural environment). In some embodiments, a population of stem cells refers to an in vivo population present in, for example, a stem cell niche that interacts with the stem cells to regulate cell fate. A "niche" may refer to a specific anatomic location that regulates how stem cells participate in tissue generation, maintenance and repair. During embryonic development, various niche factors (e.g., genes, proteins, growth factors) act on stem cells to alter gene expression, and induce their proliferation or differentiation. Stem cell niches maintain adult stem cells in a quiescent state, but after tissue injury, for example, the surrounding micro-environment actively signals to stem cells to either promote self-renewal or differentiation to form new tissues.

As used herein, cellular "differentiation" refers to the process by which a less specialized cell becomes a more specialized cell type. A cell that is able to differentiate into all cell types of the adult organism is a pluripotent cell.

As used herein, cellular "proliferation" refers to an increase in the number of cells of a population as a result of cell growth and cell division.

The stem cells referred to herein (e.g., pluripotent stem cells) may be contacted with an agent that inhibits Dis3l2. Such contact may be achieved through cell transfections techniques, many of which are known in the art. Transfection is a procedure that introduces foreign nucleic acids into cells to produce genetically modified cells. Transfection may be biological, chemical or physical. The introduced nucleic acids (DNAs and RNAs) may exist in cells either stably or transiently depending on the nature of the nucleic acids. For stable transfection, introduced nucleic acids that usually have a marker gene for selection (transgenes) are integrated into the host genome and sustain transgene expression even after host cells replicate. In contrast to stably transfected nucleic acids, transiently transfected nucleic acids are only expressed for a limited period of time and are not integrated into the genome. Transiently transfected genetic materials can be lost by environmental factors and cell division, so the choice of stable or transient transfection depends on the object of the application. Stable and/or transient transfection may be used in accordance with the present disclosure.

EXAMPLES

Example 1: Identification of Dis3l2 as a Candidate Pre-let-7 Ribonuclease

Figure 1B:
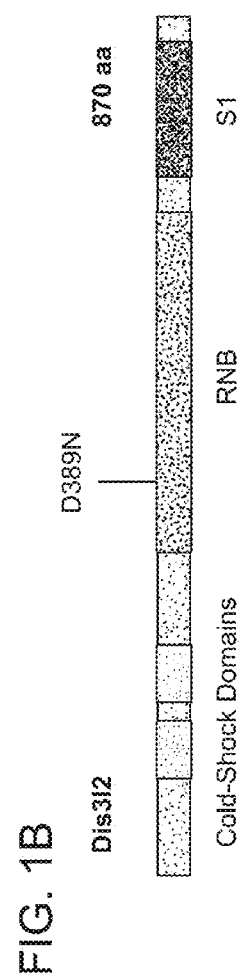
Figure 1C:
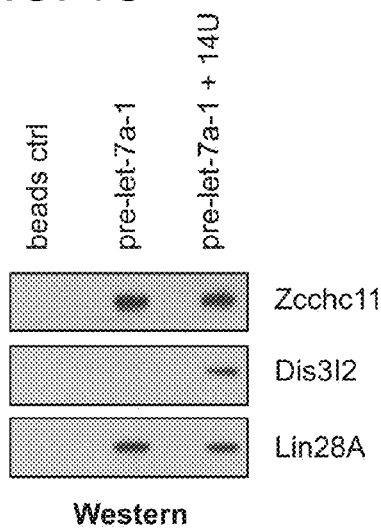
Figure 1D:
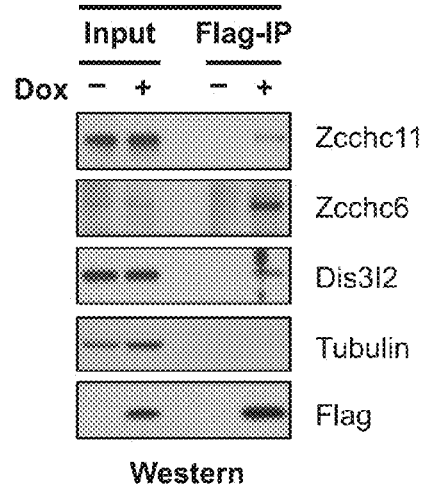

The current model for the Lin28A-mediated blockade of let-7 biogenesis involves pre-let-7 uridylation by Zcchc11 (and Zcchc6) followed by the degradation of these uridylated miRNA precursors by an unknown nuclease. Work described herein was carried out to identify the downstream nuclease(s) and a biochemical approach was used to isolate factors that specifically associate with uridylated pre-let-7 (FIG. 1a). Synthetic pre-let-7 or pre-let-7 with an oligouridine 3' extension (pre-let-7+14U) were conjugated to agarose beads and incubated with whole-cell extracts prepared from mouse embryonal carcinoma (P19) cells. The beads were washed and the associated proteins were eluted and subjected to SDS-polyacrylamide gel electrophoresis (SDS-PAGE) followed by colloidal staining (FIG. 1b). Sections of the gel were excised and subjected to mass spectroscopic sequencing. This analysis identified Lin28A and Zcchc11 that were associated with both RNAs, but not in the beads alone control. Dis3l2 [DIS3 mitotic control homolog (S. cerevisiae)-like 2], an exonuclease, was specifically detected in the pre-let-7+14U purification and not with either pre-let-7 or beads alone control (FIG. 1a). Dis3l2 protein contains characteristic ribonuclease domains and belongs to a family of 3'-5' exonucleases (FIG. 1b) (Astuti et al., 2012). These mass spec data were confirmed by Western blot analysis of the affinity-purified complexes (FIG. 1c). Co-immunoprecipitation assays performed using a mouse ESC line expressing Dox-inducible Flag-Lin28 transgene revealed that Zcchc11, Zcchc6, as well as Dis3l2, are detectable by Western blot in the Flag-Lin28A affinity eluate (FIG. 1d). These results implicate Dis3l2 as a possible nuclease in the Lin28-let-7 regulatory pathway.

Figure 1E:
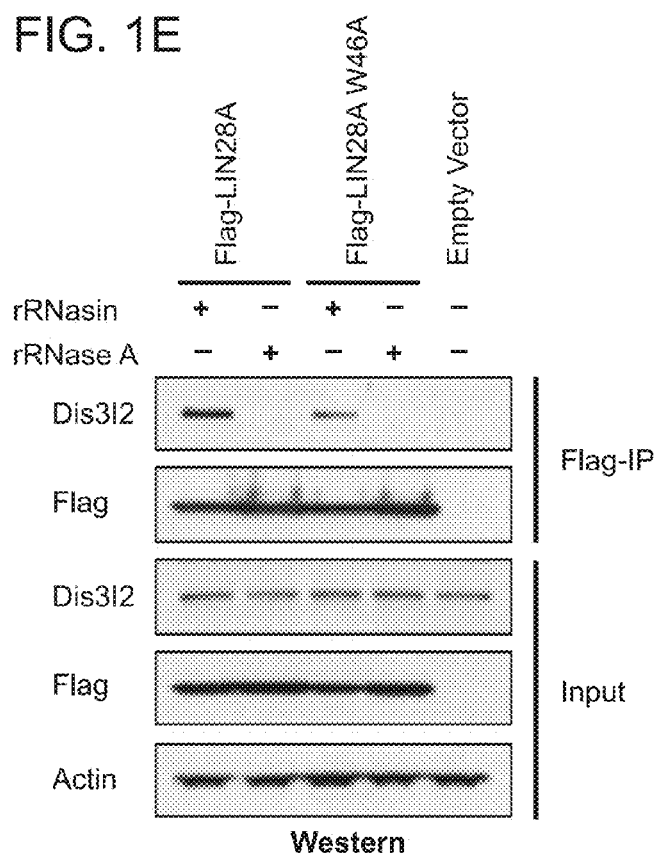

To address whether this interaction between Lin28 and Dis3l2 is mediated through RNA Applicant performed additional co-immunoprecipitation experiments using either Flag-tagged wild-type Lin28 protein or Lin28 W46A, a mutant harboring a single amino acid substitution in the cold-shock domain that exhibits compromised RNA binding activity towards pre-let-7[24]. Applicant found less Dis3l2 associated with the Lin28 W46A than wild-type Flag-Lin28. Co-immunoprecipitation was also done in the presence of either recombinant RNase A or RNase inhibitor. Lin28A-Dis3l2 interaction was strongly reduced upon RNase A treatment (FIG. 1e). Overall these results indicate that Lin28A interacts with Dis3l2 in a RNA-dependent manner and implicate Dis3l2 as a possible nuclease in the Lin28-let-7 regulatory pathway.

Figure 5A:
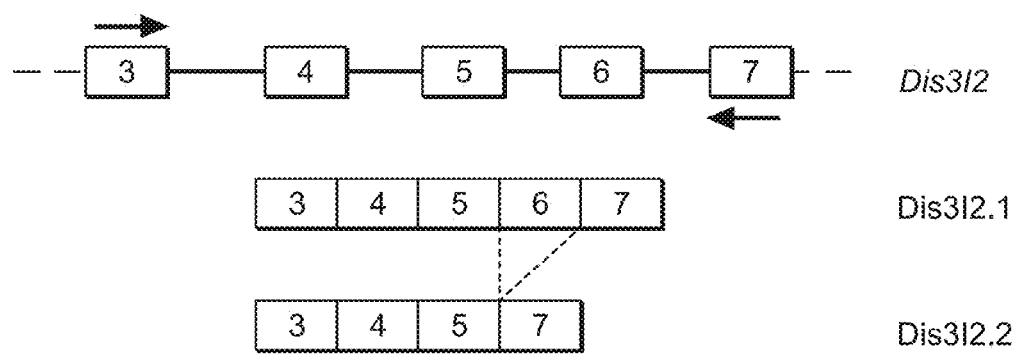
FIG. 5. Dis3l2.2 is the major transcript variant in V6.5 mouse ES cells. (a) Schematic representation of the region encompassing exon 3 to 7 of Dis3l2 gene, Dis3l2.1 and Dis3l2.2 transcript variants. Arrows indicate specific primers used in (b) for RT-PCR analysis. (b) RT-PCR analysis of Dis3l2 transcript variants. MW: molecular weight (bp: base pair); RT: reverse transcriptase.
Figure 5B:
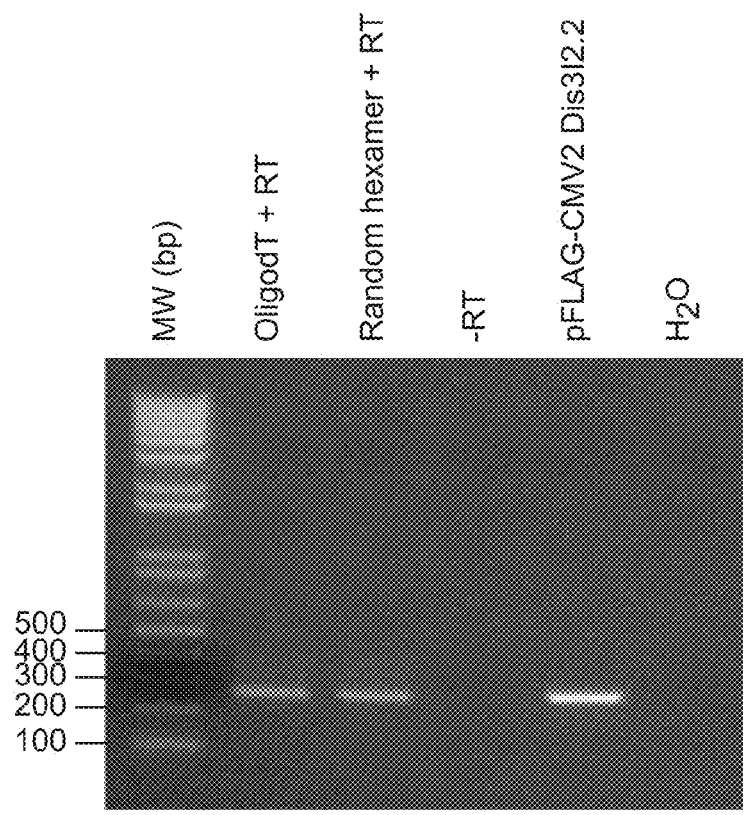
Figure 6:
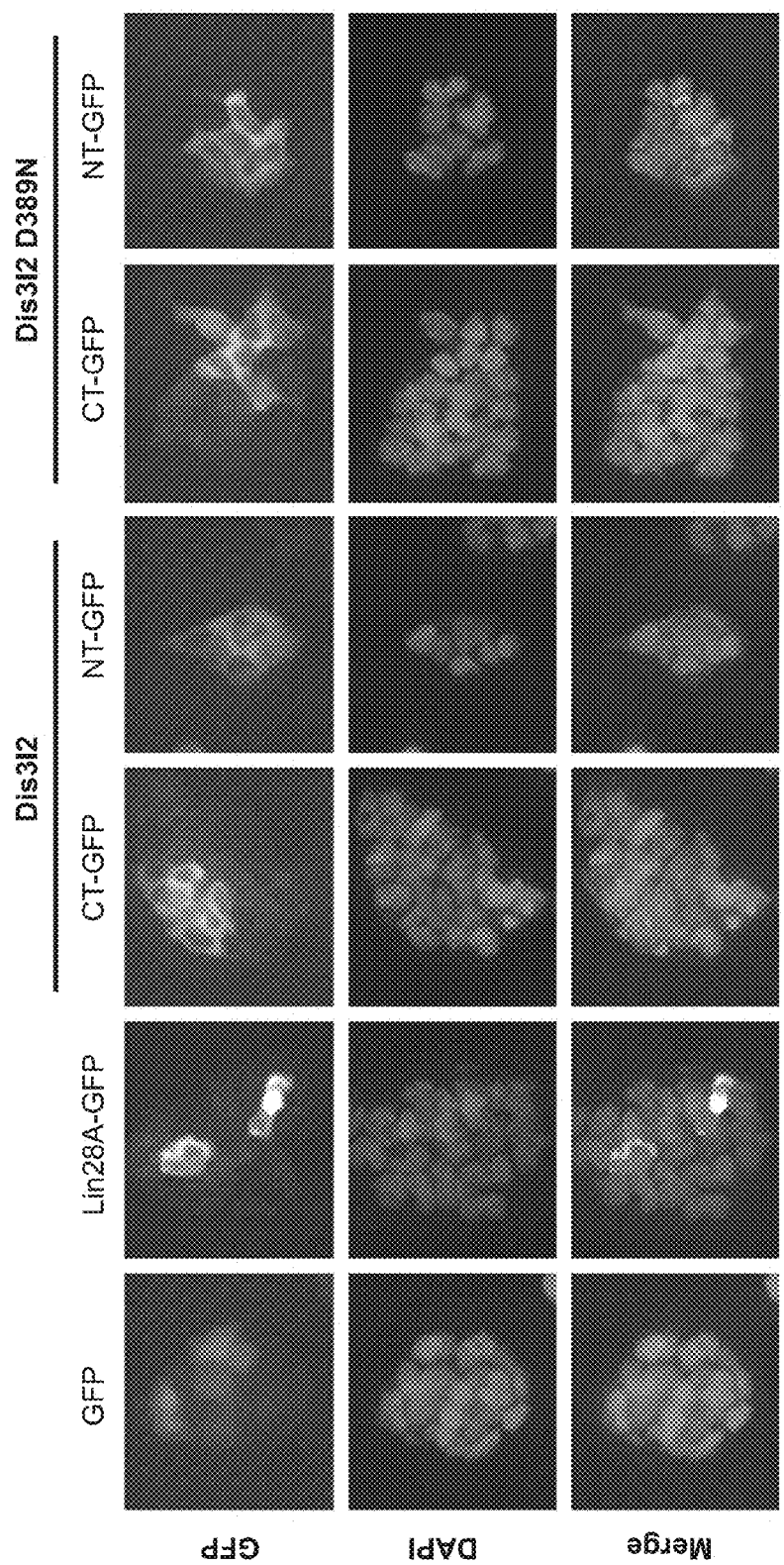
FIG. 6. Dis3l2 localizes primarily in the cell cytoplasm. Fluorescence microscopy images of V6.5 ESC expressing GFP, Lin28A-GFP, wild type Dis3l2 or D389N mutant fused to either GFP in N-terminus (NT-GFP) or C-terminus (CT-GFP) is shown. DNA was stained with DAPI.

Applicant next cloned and sequenced the major splice isoform of mouse Dis3l2 cDNA from V6.5 ESCs. The Dis3l2 gene contains 22 exons and encodes for two transcript variants, Dis3l2.1 and Dis3l2.2. While every exon is retained in Dis3l2.1 transcript, exon 6 is skipped in Dis3l2.2 encoding a slightly smaller protein of 870 amino acids compared to 884 from Dis3l2.1 transcript (FIG. 1b). RT-PCR analyses confirmed that Dis3l2.2 is the major transcript variant expressed in V6.5 ESC (FIG. 5). Since pre-let-7 degradation occurs in the cell cytoplasm Applicant next examined the subcellular localization of Dis3l2 in ESCs. They generated constructs expressing Dis3l2 with either an N-terminal or C-terminal GFP fusion and monitored GFP localization by fluorescence microscopy (FIG. 6). This revealed that both wild type and catalytically impaired Dis3l2 proteins are primarily localized to the cytoplasm of V6.5 ESC, which is consistent with the reported DIS3L2 localization in other cell types[28].

Dis3l2 Preferentially Degrades Uridylated Pre-Let-7 In Vitro.

To examine Dis3l2 substrate specificity Applicant carried out RNA degradation assays using affinity-purified Flag-Dis3l2 and $^{32}$P 5'-end labeled pre-miRNAs. Reaction products were resolved on a denaturing polyacrylamide gel and ribonuclease activity was monitored by autoradiography. Dis3l2 was found to preferentially degrade pre-let-7+14U over non-uridylated pre-let-7 or an unrelated pre-miR-21 (FIG. 2a). To rule out the possibility that this observed activity was due to a co-purifying nuclease in the Flag-Dis3l2 IP, Applicant generated a mutant Dis3l2-expressing construct by replacing a conserved Aspartic Acid residue in the catalytic domain with an Asparagine (D389N) (FIG. 1b). The equivalent aspartate at position 389 in the human DIS3L1 RNB domain is critical for its exonuclease activity. Mutation of this residue abolishes the exonuclease activity without interfering with RNA binding (Staals et al., 2010). In contrast to wild-type Flag-Dis3l2, which displayed robust degradation of pre-let-7+14U, no activity was detected with the catalytic mutant version of the protein (FIG. 2b). A more quantitative analysis revealed that affinity-purified Dis3l2 displayed preferential activity towards pre-let-7+14U than on the non-uridylated pre-let-7 (FIG. 2c).

Dis3l2 is Necessary and Sufficient for the Preferential Degradation of Uridylated pre-let-7 in Vitro.

Figure 2E:
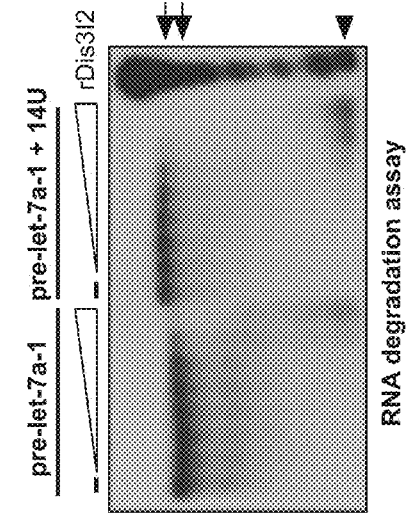
FIG. 2. Dis3l2 preferentially degrades uridylated pre-let-7. (a) Flag-Dis3l2 purified from transiently transfected V6.5 ESCs was incubated with radiolabeled synthetic pre-miR-21, pre-let-7a-1, or pre-let-7a-1+14U RNA. Where indicated, 100 ng of total RNA from ESCs was included in the reactions to reduce non-specific RNA degradation. (b) Flag-tagged Dis3l2 or catalytically impaired Dis3l2 D389N was purified from transiently transfected V6.5 ESCs (upper panel) and titrated for RNA degradation assay on synthetic pre-let-7a-1+14U RNA (lower panel). 100 ng of total RNA from ESCs was included in each reaction. (c) RNA degradation assay showing the effect of Flag-Dis3l2 titration on synthetic pre-let-7a-1 or pre-let-7a-1+14U RNA. 1000 ng of total RNA from ESCs was included in each reaction. For (a), (b), and (c), arrows indicate the positions of the full-length radiolabeled RNA while arrowhead indicates the degraded products. (d) Recombinant His-Dis3l2 (indicated by arrow) was affinity-purified from BL-21 *E. coli* and examined by SDS-PAGE and Coomassie blue staining (upper panel). Western blotting confirms the peak of Dis3l2 elution (lower panel). (e) Titration of Flag-Dis3l2 from 293T (IP eluate) and of His-Dis3l2 from *E. coli* (recombinant) were analyzed by Western blotting (upper panel), and their activity on synthetic pre-let-7a-1+14U RNA was examined by RNA degradation assays (lower panel). 250 ng of total RNA from ESCs was included in the reactions. (f) Titration of His-Dis3l2 from *E. coli* was incubated with synthetic pre-let-7a-1 or pre-let-7a-1+14U RNA. 1000 ng of total RNA from ESCs was included in the reactions. For (b) and (c), arrows indicate the positions of the full-length radiolabeled RNA while arrowhead indicates the degraded products. (g) Representative time course assay. Degradation experiments were carried out as in figure (f) with samples collected at the indicated time points. (h) Quantitation of three independent experiments as in (g) with the corresponding calculated half-lives of pre-let-7a-1 and pre-let-7a-1+14U. $p<0.01$ [two-way analysis of variance (ANOVA) test].
Figure 2F:
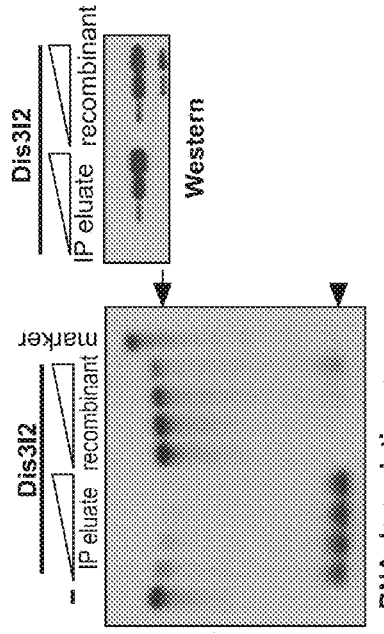
Figure 2G:
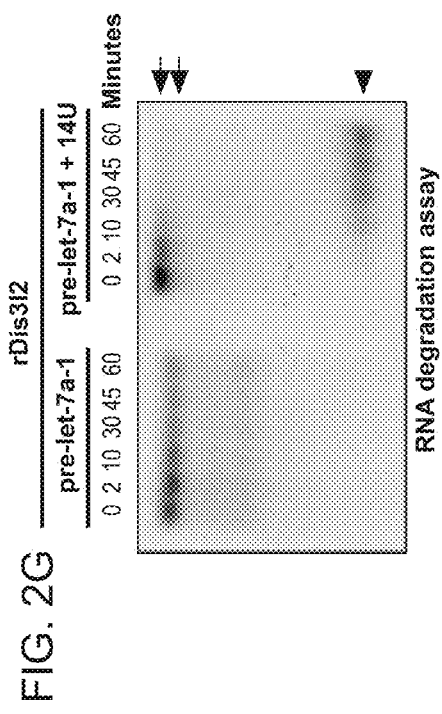
Figure 2H:
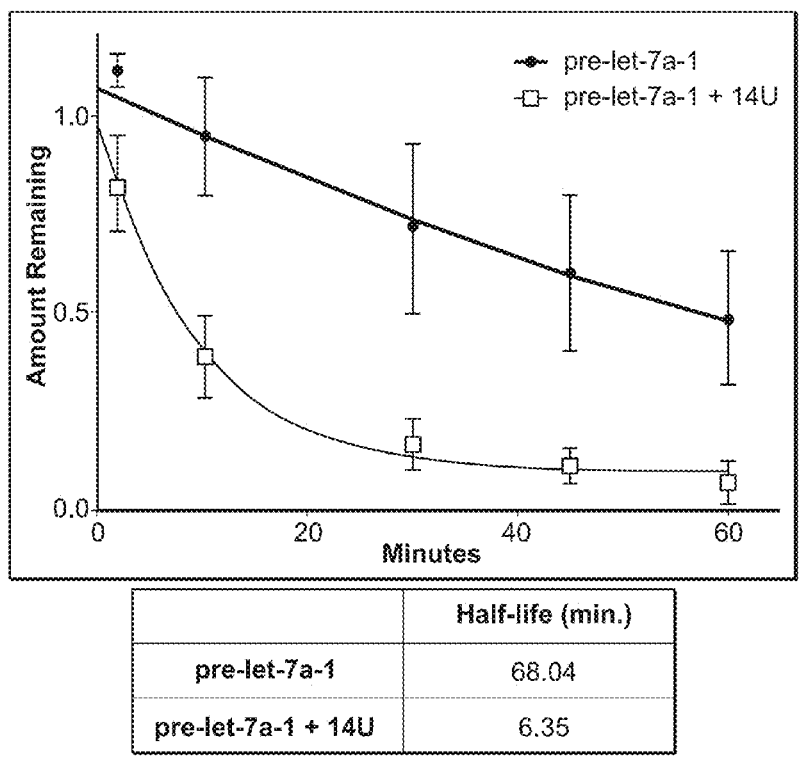
Figure 7A:
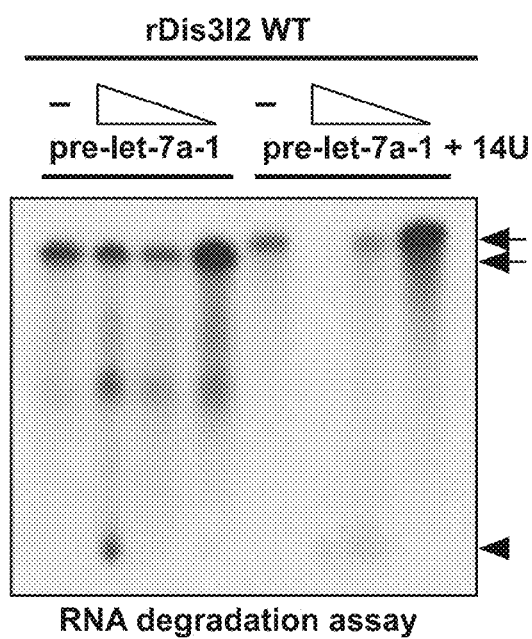
FIG. 7. Characterization of recombinant Dis3l2. (a) Top panel, bacterially expressed 6x-His Dis3l2 preferentially degrades synthetic uridylated pre-let-7a-1. Middle panel, as above except D389N mutant 6x-His Dis3l2 lacks detectable exonuclease activity was used as a control. Bottom panel, Western blot analysis of wild-type (WT) and catalytically inert (D389N) recombinant Dis3l2 used in the RNA degradation assays. (b) Recombinant Dis3l2 binds to uridylated pre-let-7a-1 but not WT pre-let-7a-1 by Electrophoretic Mobility Shift Assay (EMSA). Recombinant Lin28, which binds to the loop of let-7 pre-miRNAs is used as a positive control.
Figure 7A:
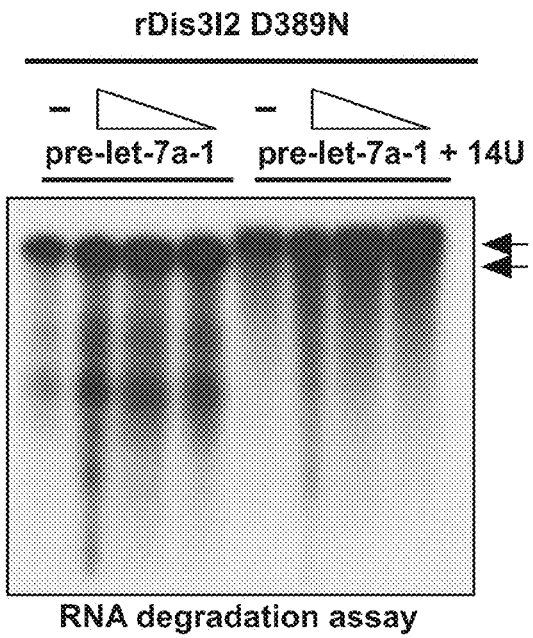
Figure 7A:
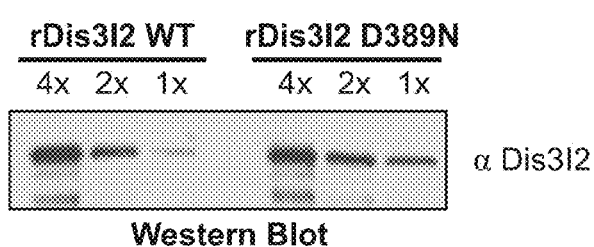
Figure 8A:
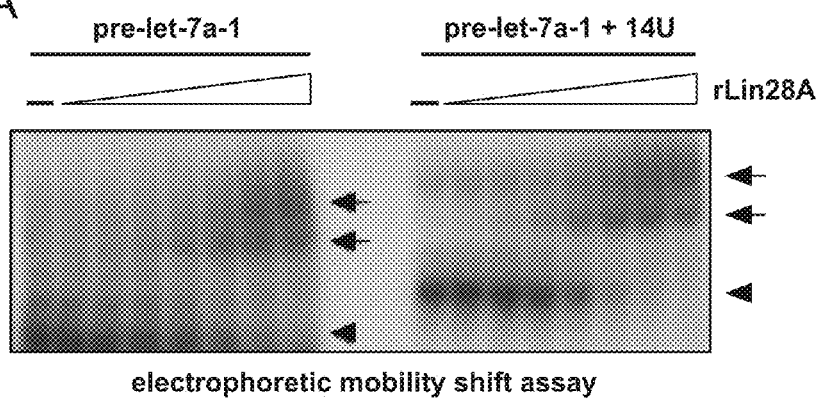
FIG. 8. Lin28A does not contribute to Dis3l2 exonuclease activity (a) Titration of recombinant Lin28A was incubated with synthetic pre-let-7a-1 or pre-let-7a-1+14U RNA, and the binding activity was monitored by EMSA. Arrowheads indicate the positions of the full-length radiolabeled RNA, and arrows indicate the formed Lin28A-RNA complexes. (b) The effect of Lin28A titration on Dis3l2 degradation of synthetic pre-let-7a-1 or pre-let-7a-1+14U RNA was monitored by RNA degradation assays.
Figure 8B:
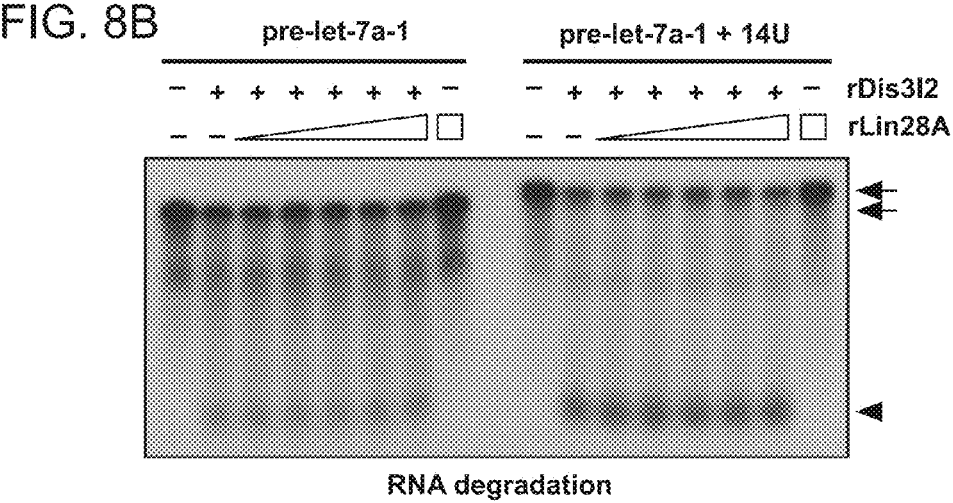

Next, to determine whether Dis3l2 is sufficient for the selective degradation of uridylated pre-let-7 recombinant Dis3l2 protein was generated in E. Coli. His-Dis3l2 was purified and analyzed by Coomassie blue staining and Western blot (FIG. 2d). Although the activity of recombinant Dis3l2 (rDis3l2) was lower than that of the affinity-purified Flag-Dis3l2 complexes, there was a similar preference for pre-let-7+14U compared with the non-uridylated pre-let-7 using the recombinant Dis3l2 protein (FIGS. 2e, and 2f). To rule out the possibility that this observed activity was due to a bacterial nuclease that might co-purify with His-Dis3l2 Applicant generated a mutant (D389N) rDis3l2 and confirmed that this catalytic mutant displayed no ribonuclease activity in these assays (FIG. 7a). Considering that uridylated pre-let-7a-1 was previously found associated with Flag-Lin28A protein complexes isolated from HEK293T cells and their data showing a physical association between Flag-Lin28A and Dis3l2 protein in ESCs, Applicant next explored whether Lin28A protein influenced Dis3l2 activity in vitro (Heo et al., 2008) and (FIG. 1e). Saturating amounts of recombinant Lin28A protein (determined by EMSA) prepared from E. Coli was added together with recombinant Disl2 in pre-let-7 degradation assays. This analysis revealed that Lin28A had no effect on Dis3l2 activity in vitro (FIG. 8). Next, to more quantitatively measure the substrate preference of Dis3l2 for uridylated pre-let-7 Applicant performed time course experiments with rDis3l2. This analysis revealed a strong preference for the degradation of uridylated pre-let-7 compared to non-uridylated pre-let-7, with >10-fold difference in the relative RNA stability in these assays (FIGS. 2g and 2h). Together these results reveal that purified recombinant Dis3l2 preferentially degrades uridylated pre-let-7 in vitro and the oligoU-tail serves as a decay signal for this ribonuclease.

Figure 3A:
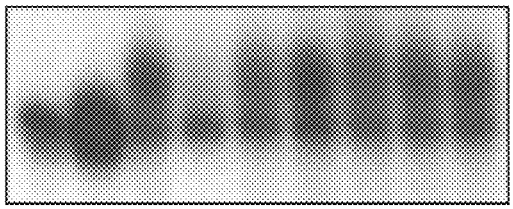
FIG. 3. Molecular determinants of Dis3l2 activity. (a) Immunopurified Flag-Dis3l2 degrades pre-let-7a-1 uridylated in vitro by Lin28A and Zcchc11. Incubation with cold competitor uridine triphosphate (lanes 3-9) facilitates the formation of longer uridine tails, which are preferred substrates for Dis3l2 but not the catalytically inactive Dis3l2 D389N. Western blot analysis indicating similar amounts of Flag-immunopurified Dis3L2 protein is shown in FIG. 2c. (b) RNA degradation assays performed using uniformly labeled in vitro transcribed pre-let-7 RNAs with different 3' ends as indicated. RNAs were incubated in the presence or absence of rDis3l2. (c) Schematic representation of different Dis3l2 truncation mutants (DN: N-terminus deletion; DC: C-terminus deletion; RNB: both N and C-terminus deletion). Western blot analysis of immunoprecipitated FLAG-tagged proteins used in (c) and (d). Titration corresponds to 1, 2 and 4 times dilutions. (d) RNA degradation assay assessing the exonuclease activity of wild type Dis3l2, D389N mutant and different truncation mutants on synthetic pre-let-7a-1+14U RNA using 15% polyacrylamide denaturing gel. (e) Gel shift analyses assessing the RNA binding activity of wild type Dis3l2, D389N mutant and different truncation mutants on synthetic pre-let-7a-1+14U RNA using 4-20% polyacrylamide native gel.

To further explore the functional relationship between Lin28, TUTase activity, and Dis3l2-mediated RNA degradation Applicant performed in vitro reconstitution assays. Previously we showed that Lin28 enhances the uridylation activity of Zcchc11 (and Zcchc6) towards pre-let-7. In these assays TUTase activity was measured by the incorporation of radiolabeled UTP[26,27]. However due to the limiting concentration of UTP the oligo-U tails added in these reactions are short, comprising only a few nucleotides. Indeed supplementing such reactions with additional (non-radiolabeled) UTP leads to the generation of longer U-tails (FIG. 3a, compare lanes 1, 2, and 3). Interestingly, addition of Dis3l2 (but not the catalytically inactive mutant Dis3l2) leads to the selective degradation of the pre-let-7 with longer U-tails (FIG. 3a). These data biochemically define the minimal set of proteins and enzymes required to recapitulate the selective degradation of pre-let-7 observed in vivo, and raise important questions regarding U-tail length requirements to stimulate Dis3l2-mediated degradation in vitro. To address this we prepared a panel of pre-let-7 RNA substrates with varying U-tail lengths and monitored Dis3l2 degradation activity. This analysis revealed that tails of at least 10 uridines stimulates Dis3l2 activity with maximal stimulation observed with U-tails of 14 or greater. This result is consistent with the pre-let-7 RNAs associated with Lin28A-containing ribonucleoprotein complexes isolated from cells that were found to have an average tail length of 14 uridines[8].

Figure 3B:
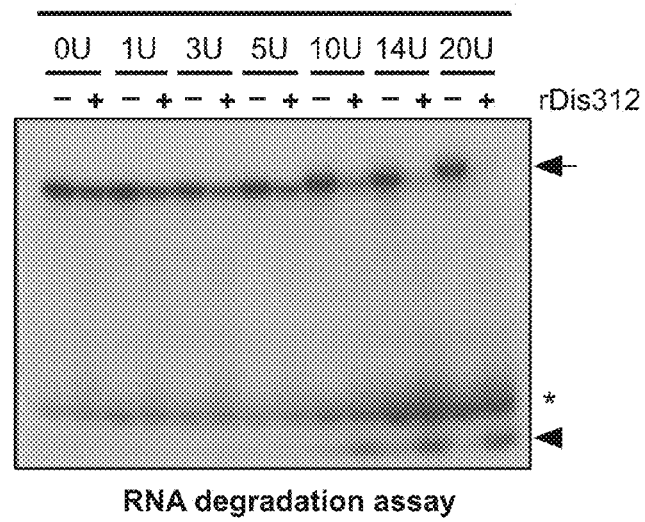
Figure 3C:
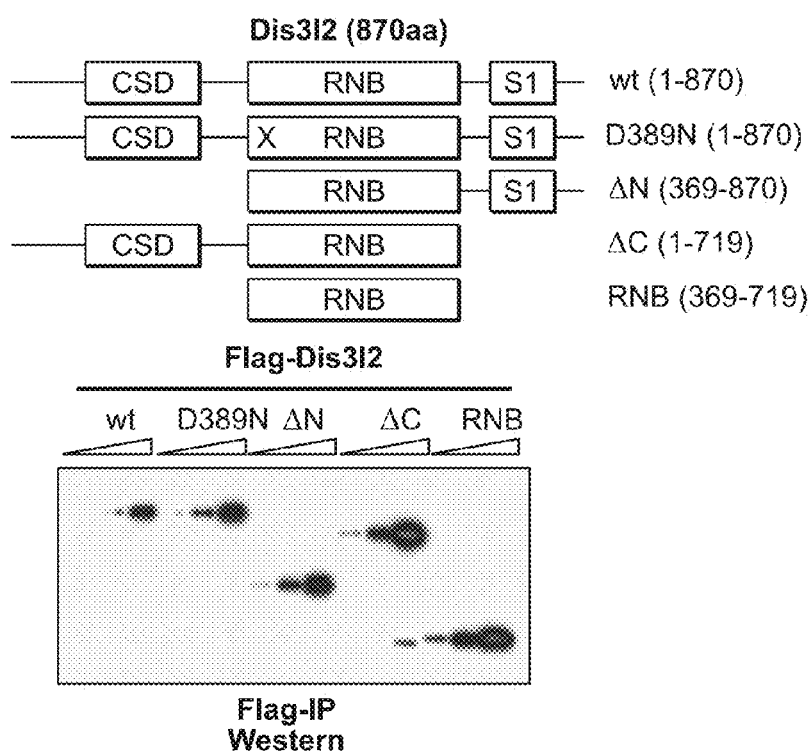
Figure 3D:
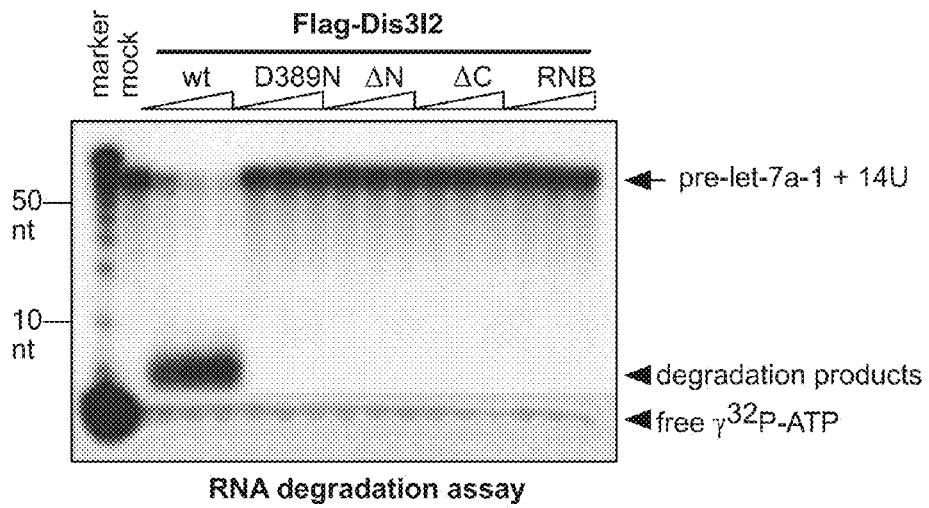
Figure 3E:
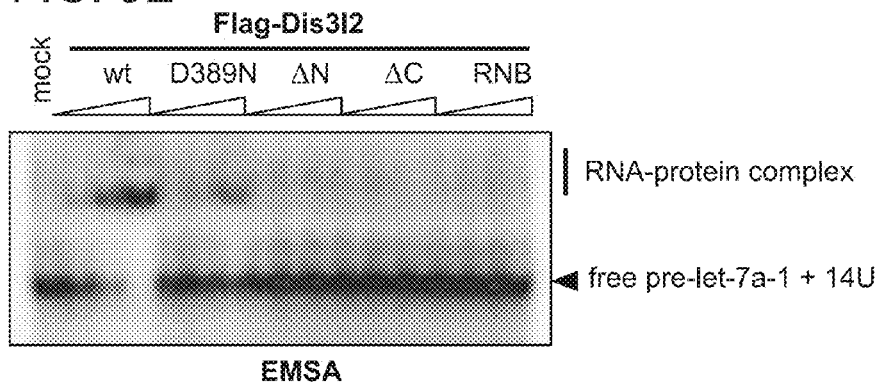
Figure 7B:
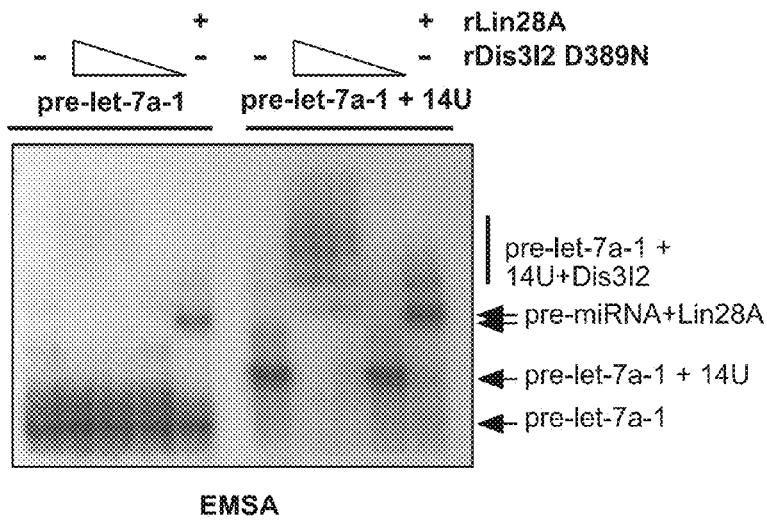

To examine the Dis3l2 domain requirements we generated three deletion mutants lacking either the N-terminus, C-terminus, or both N and C-terminal regions (FIG. 3d). RNA degradation assays and electromobility shift assays (EMSA) revealed that truncation of either the N- or the C-terminus region abrogated both Dis3l2 binding and nuclease activities on uridylated pre-let-7 RNA (FIGS. 3e and 3f). This suggests that both the cold-shock domain(s) as well as the S1 domain are required for binding to uridylated pre-let-7. Though the catalytic mutant (D389N) Dis3l2 was inactive in RNA degradation assays it retained the ability selectively bind to uridylated pre-let-7 (FIG. 3f and FIG. 7b).

Depletion of Dis3l2 Causes Accumulation of Uridylated pre-let-7 in Embryonic Stem Cells.

Figure 4A:
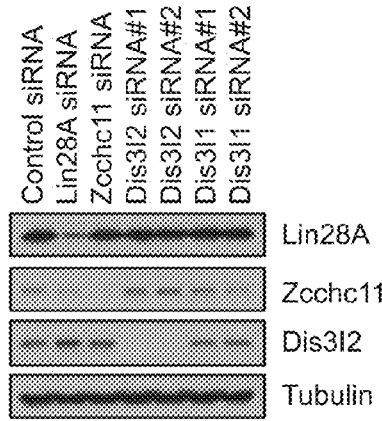
FIG. 4. Dis3l2 is required for degradation of uridylated pre-let-7 in embryonic stem cells. (a) Whole-cell extracts from V6.5 ESCs transfected with control, Lin28A, Zcchc11, Dis3l2, or Dis3l1 siRNA were examined by Western blotting. (b)(c) Levels of Dis3l1 mRNA (b), mature let-7a, let-7g, let-7i, and miR-21 (c) from the samples in (a) were analyzed by quantitative RT-PCR. Error bars±S.D. (n=3). (d) Levels of mature let-7g and let-7a were analyzed by Northern blotting. Total RNA stained by ethidium bromide indicates an equal loading of the samples. (e) Titration of recombinant Dicer was incubated with synthetic pre-let-7a-1 or pre-let-7a-1+14U RNA. Arrows indicate the positions of the full-length radiolabeled RNA while arrowhead indicates the products processed by Dicer. (f)(g) 1 µg of total RNA from the samples in (a) was fractionated into >200 nt and <200 nt long RNA. RT was performed using oligo(dA)12 and levels of cDNA from the endogenous pre-let-7 (f) or pri-let-7 (g) RNA were quantitated by real-time PCR. Error bars±S.D. (n=3). (h) Whole-cell extracts from V6.5 ESCs expressing shRNA, or shRNA together with plasmid (empty vector, Dis3l2 WT, Dis3l2 D389N) or siRNA (control siRNA, Dis3l1 siRNA), as indicated, were examined by Western blotting. (i) Levels of Dis3l1 mRNA from the samples in (i) were analyzed by quantitative RT-PCR. Error bars±S.D. (n=3). (j) Levels of pre-let-7g from the samples in (i) were analyzed by Northern blotting and q.RT-PCR (FIG. S3).
Figure 4B:
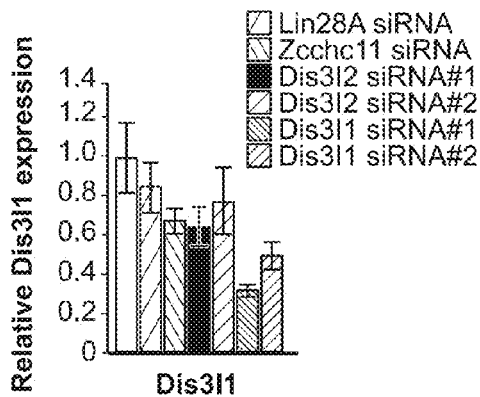
Figure 4C:
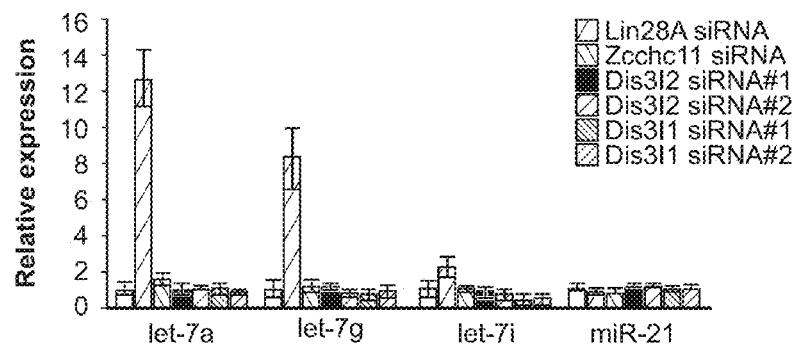
Figure 4D:
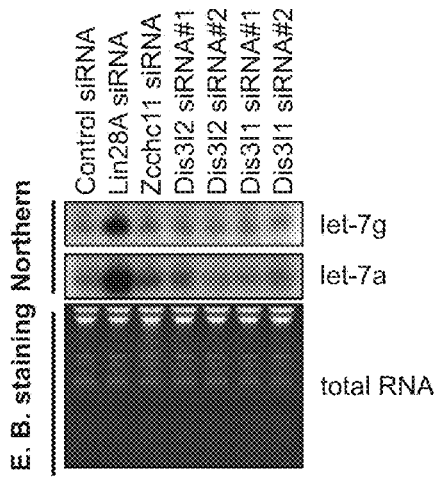
Figure 4E:
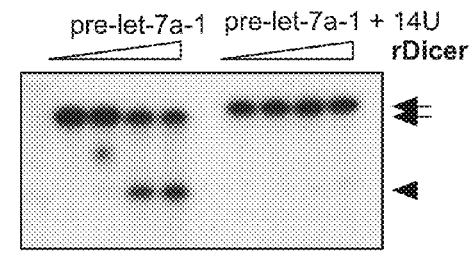
Figure 4F:
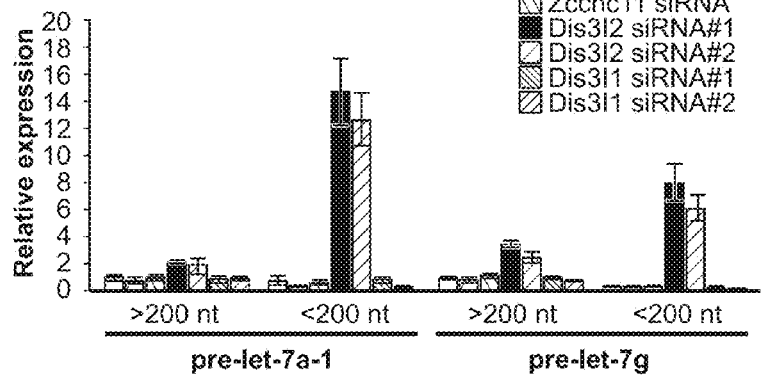
Figure 4G:
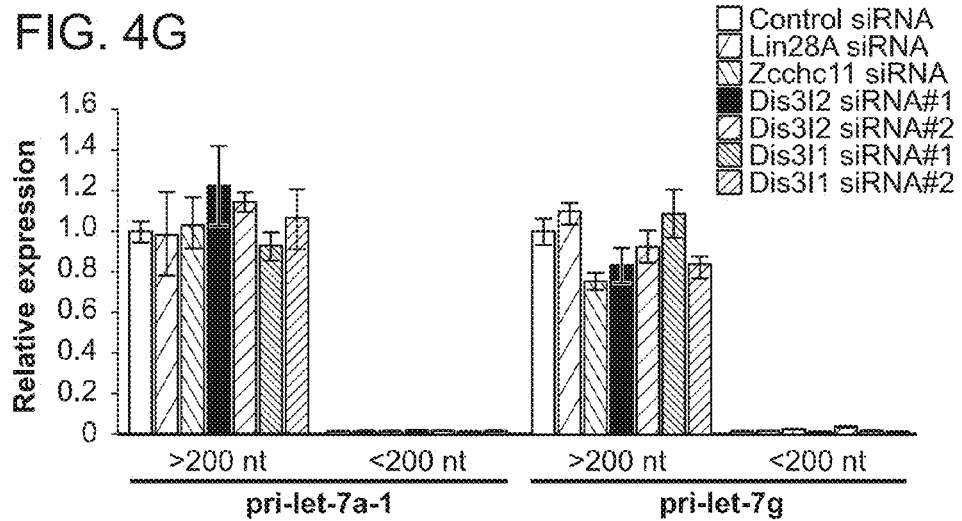
Figure 9A:
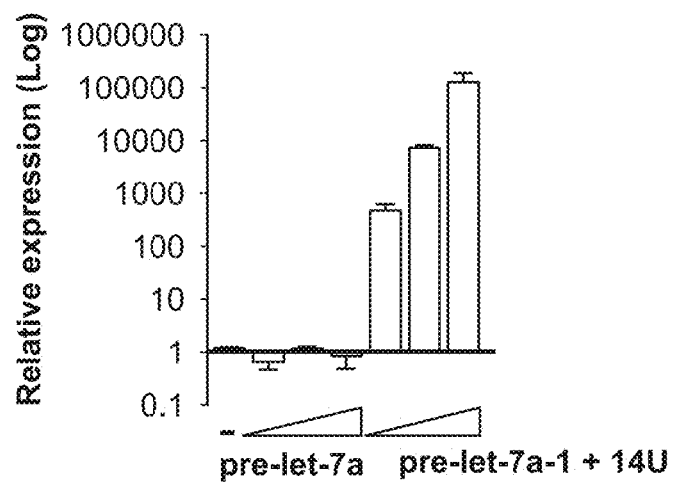
FIG. 9. Validation of quantitative RT-PCR. (a) 500 ng of total RNA from DGCR8-null V6.5 ESCs was fractionated for <200 nt long RNA then spiked with 0.1 pg, 1 pg, or 10 pg of synthetic pre-let-7a-1 or pre-let-7a-1+14U RNA. RT was performed using oligo(dA)12 and levels of cDNA from the spiked RNA were quantitated by real-time PCR. Error bars±S.D. (n=3). (b) The quantitative RT-PCR products from V6.5 Dis3l2 knockdown cells for pri-let-7a-1, pre-let-7a-1, pri-let-7g, pre-let-7g, U6, and ACTB were resolved on 2% agarose gel. The predicted size for each PCR product is indicated. (c) The products were sequenced and blasted to confirm the correct PCR amplification.
Figure 9B:
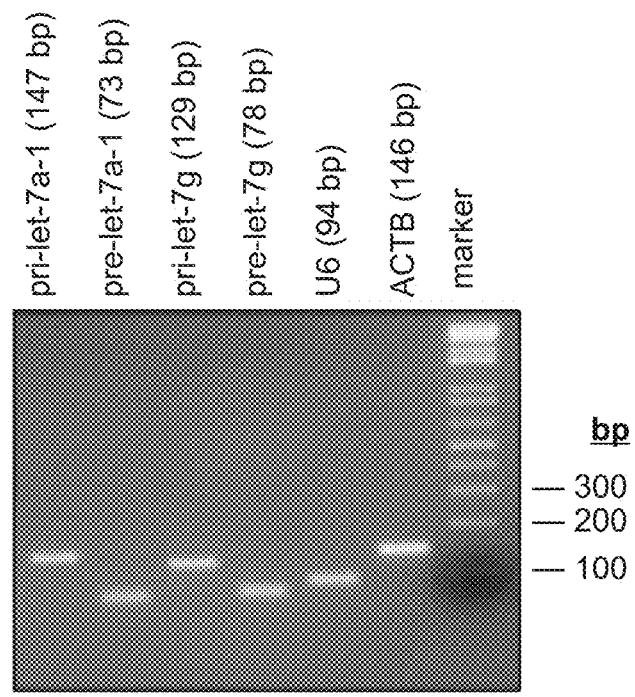

The role of Dis3l2 in the let-7 miRNA regulatory pathway was assessed using siRNAs to deplete Dis3l2 expression in mouse ESCs. Two individual siRNAs that gave a substantial Dis3l2-depletion were selected (FIG. 4a). Lin28A and Zcchc11 siRNAs were used as controls. Knockdown of the respective genes was verified by Western blot (FIG. 4a). siRNAs that target a related family member Dis3l1 were also included and their use confirmed knockdown by quantitative reverse transcription PCR (q.RT-PCR) (FIG. 4b). Applicant monitored effects of gene knockdown on mature miRNA expression levels by q.RT-PCR. While Lin28A knockdown led to the expected dramatic accumulation of multiple let-7 miRNAs, knockdown of Dis3l2 (or Dis3l1) had no effect. However, there was a modest increase in let-7 expression in the Zcchc11-depleted samples as previously reported (Hagan et al., 2009; Heo et al., 2008; Thornton et al., 2012) (FIG. 4c). Similar results were observed by Northern blot analysis of these samples (FIG. 4d). Uridylated pre-let-7 has been previously shown to be resistant to cleavage by affinity-purified Dicer complex. Applicant found pre-let-7+14U to be a poor substrate for recombinant Dicer in processing assays. In comparison, pre-let-7 was processed by Dicer to ~22 nt duplexes (FIG. 4e). Considering that pre-let-7+14U is inefficiently processed by Dicer Applicant postulated that knockdown of Dis3l2 in cells could lead to accumulation of uridylated pre-let-7 without affecting levels of mature let-7. To test this, they developed a sensitive q.RT-PCR-based assay for the specific detection of uridylated pre-let-7. For this, Applicant used an oligo-dA primer for the reverse transcriptase first-strand cDNA synthesis step and primers complementary to pre-let-7 for detection of uridylated pre-let-7 by real-time PCR. Synthetic pre-let-7−/+14U were used to validate this assay. This approach made it possible to specifically detect uridylated pre-let-7 (FIG. 9a). This q.RT-PCR based methodology was used to investigate whether Dis3l2 knockdown leads to the accumulation of uridylated pre-let-7 in ESCs. RNA was size fractionated in order to specifically measure relative levels of uridylated pre-let-7 in the <200 nt fraction and the corresponding pri-let-7 transcripts in the large >200 nt fraction. This quantitative analysis revealed the specific accumulation of uridylated pre-let-7a-1 and pre-let-7g upon Dis3l2 knockdown (FIG. 4f), whereas levels of the corresponding pri-let-7 transcripts were unchanged (FIG. 4g). PCR products were cloned and sequenced to confirm the specificity of this PCR-based assay (FIG. 9b,c). This quantitative analysis revealed the specific accumulation of uridylated pre-let-7a-1 and pre-let-7g upon Dis3l2 knockdown (FIG. 4f), whereas levels of the corresponding pri-let-7 transcripts were unchanged (FIG. 4g). PCR products were cloned and sequenced to confirm the specificity of this PCR-based assay (FIG. 9b, 9c).

Figure 4H:
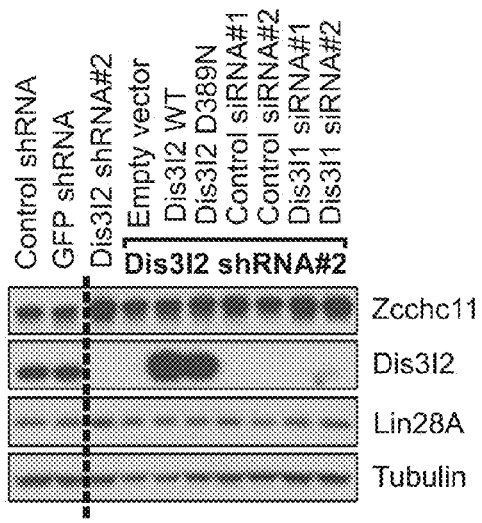
Figure 4I:
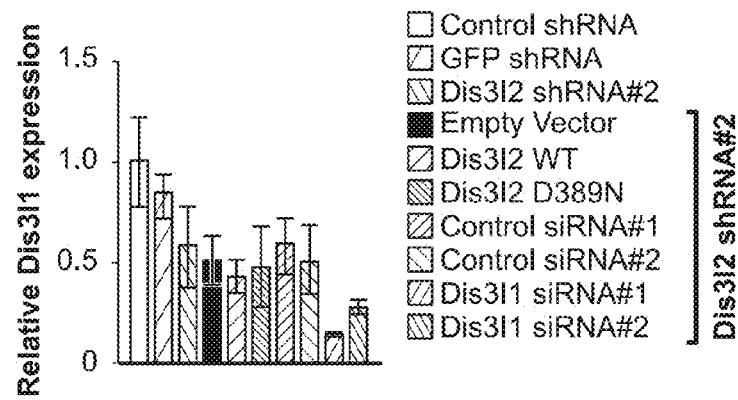
Figure 4J:
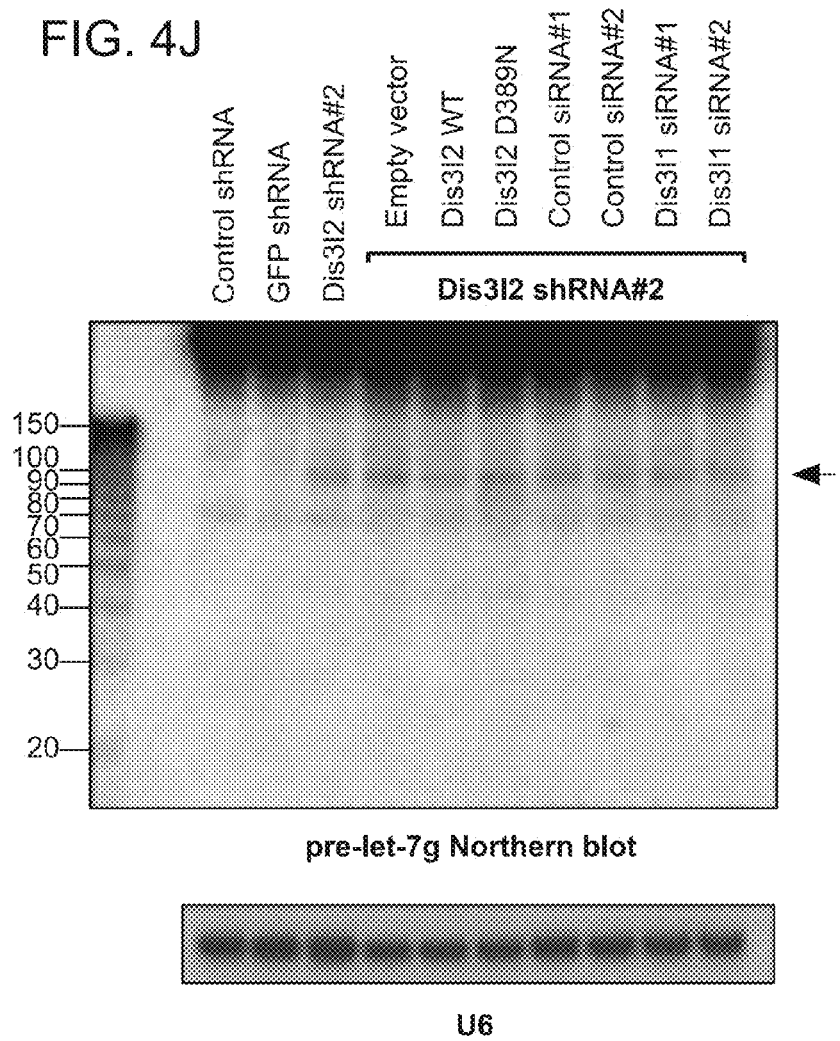
Figure 10A:
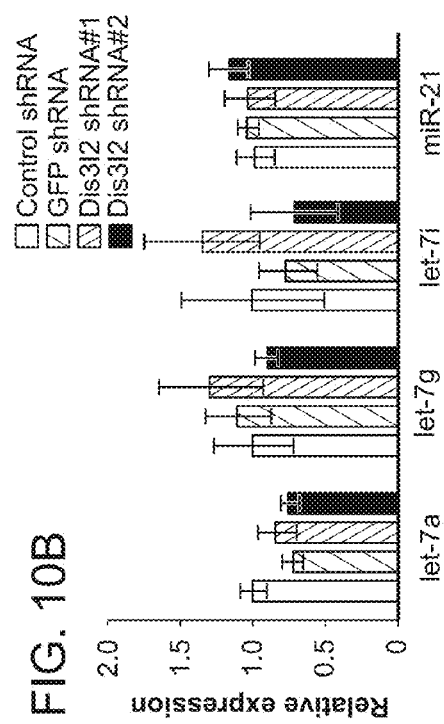
FIG. 10. Dis3l2 knockdown leads to accumulation of uridylated pre-let-7. (a) Whole-cell extracts from V6.5 ESCs expressing shRNA against control, GFP, or Dis3l2 were examined by Western blotting. (b) Levels of mature let-7a, let-7g, let-7i, and miR-21 from the samples in (a) were analyzed by quantitative RT-PCR. Error bars±S.D. (n=3). (c)(d) 1 µg of total RNA from the samples in (a) was fractionated into >200 nt and <200 nt long RNA (mirVana™ miRNA Isolation Kit). RT was performed using oligo(dA)12 on <200 nt long RNA for pre-let-7 (c), or on >200 nt long RNA for pri-let-7. Error bars±S.D. (n=3). (d). Levels of the resulting cDNA were quantitated by real-time PCR. (e) Total RNA from V6.5 and Dis3l2 shRNA#2 ESCs was fractionated into >200 nt and <200 nt long RNA. The indicated amount of synthetic pre-let-7a-1+14U and in-vitro transcribed pre-let-7g+14U was spiked into 1 µg of fractionated V6.5 RNA (for example, 0.1 pg of pre-let-7a-1+14U and 10 pg of pre-let-7g were spiked in 1 mg of fractionated V6.5 RNA). Reverse transcription was then performed using oligo(dA)12 as described in Methods. After normalized to U6, signals from 10 pg of pre-let-7a-1 or pre-let-7g were set to 100. Signals from the Dis3l2 shRNA#2 sample were fitted to a linear trend to estimate the pre-let-7 levels. (f)(g) 1 µg of total RNA from the samples in (FIG. 3i) was fractionated into >200 nt and <200 nt long RNA. RT was performed using oligo(dA)12 on <200 nt long RNA for pre-let-7 (n=3) (1) or on >200 nt long RNA for pri-let-7 (m). Levels of the resulting cDNA were quantitated by real-time PCR. Error bars±S.D. (n=3).
Figure 10B:
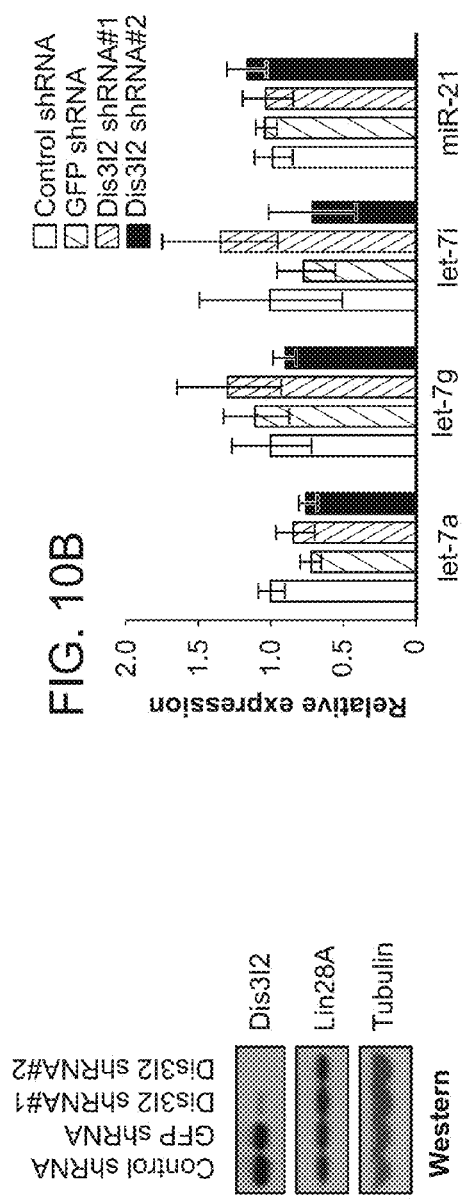
Figure 10C:
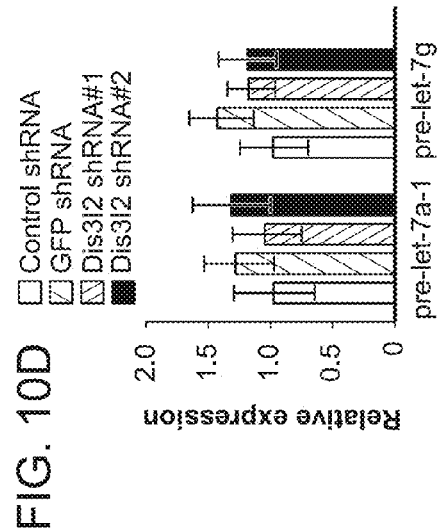
Figure 10D:
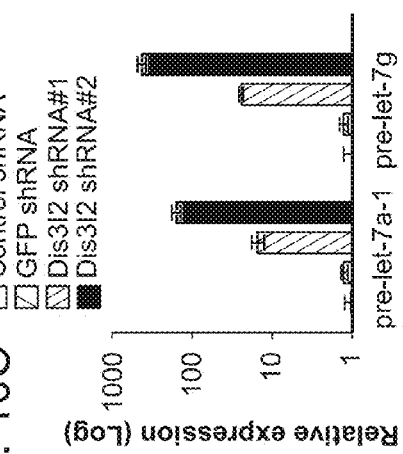
Figure 10E:
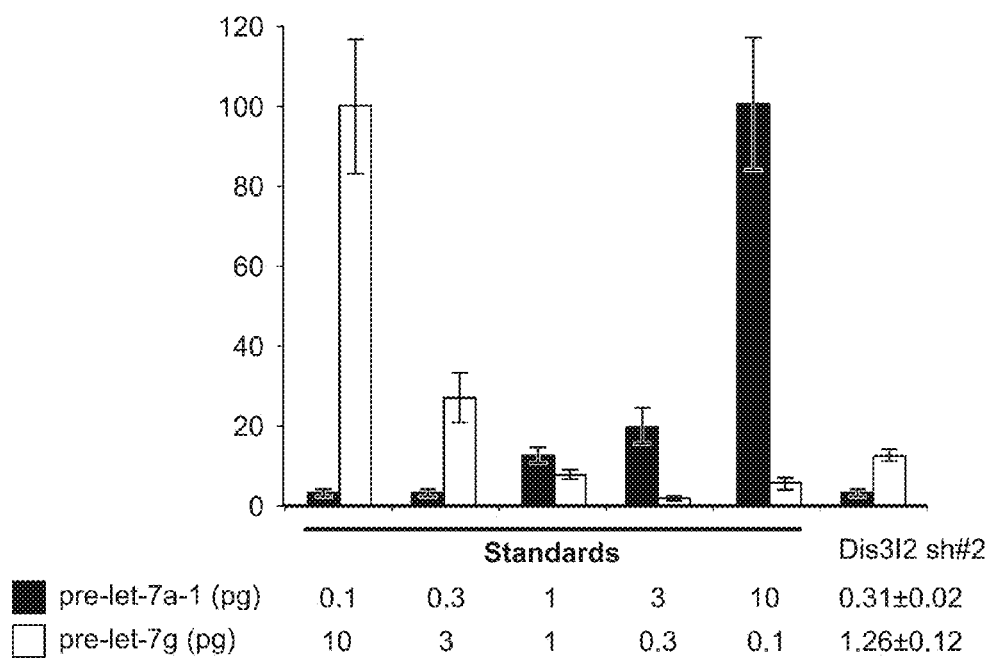
Figure 10F:
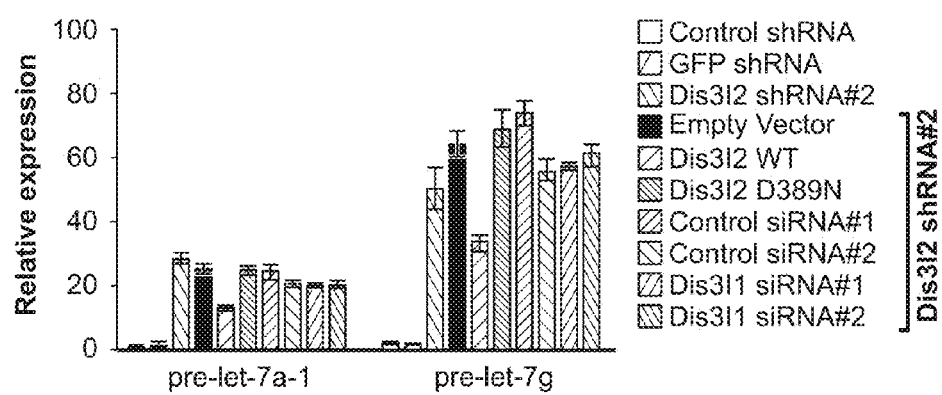
Figure 10G:
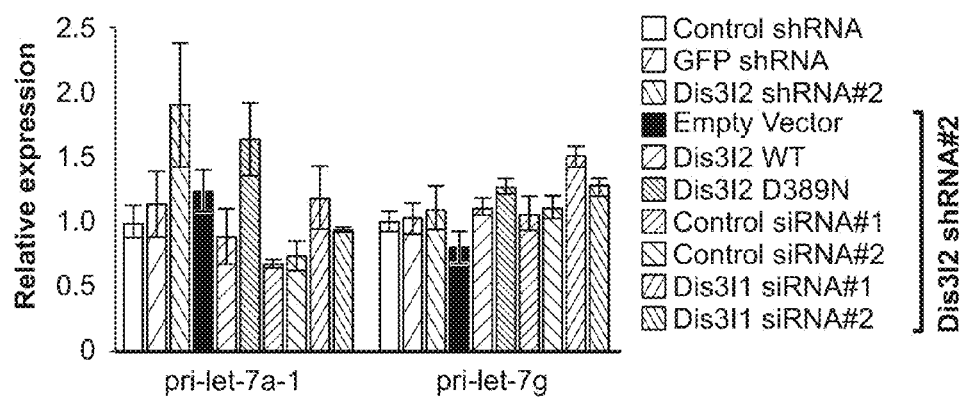
Figure 11A:
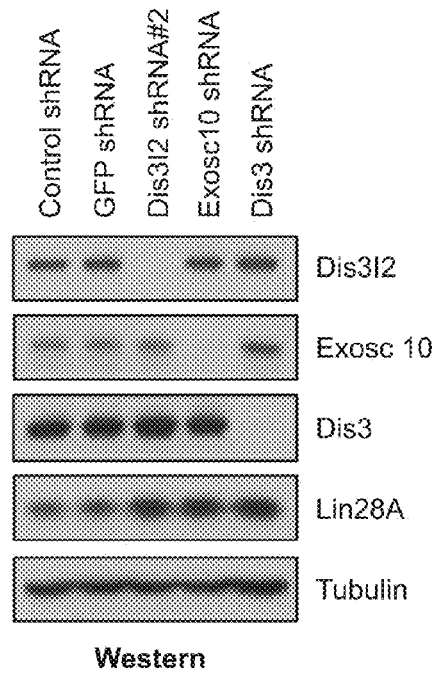
FIG. 11. Knockdown of the catalytic subunits of the exosome does not lead to accumulation of pre-let-7. (a) Whole-cell extracts from V6.5 ESCs expressing shRNA against control, GFP, Dis3l2, Exosc10, or Dis3 were examined by Western blotting. (b) 1 µg of total RNA from the samples in (a) was fractionated into >200 nt and <200 nt long RNA. RT was performed using oligo(dA)12 on <200 nt long RNA for pre-let-7. Error bars±S.D. (n=3). (d). Levels of the resulting cDNA were quantitated by real-time PCR.
Figure 11B:
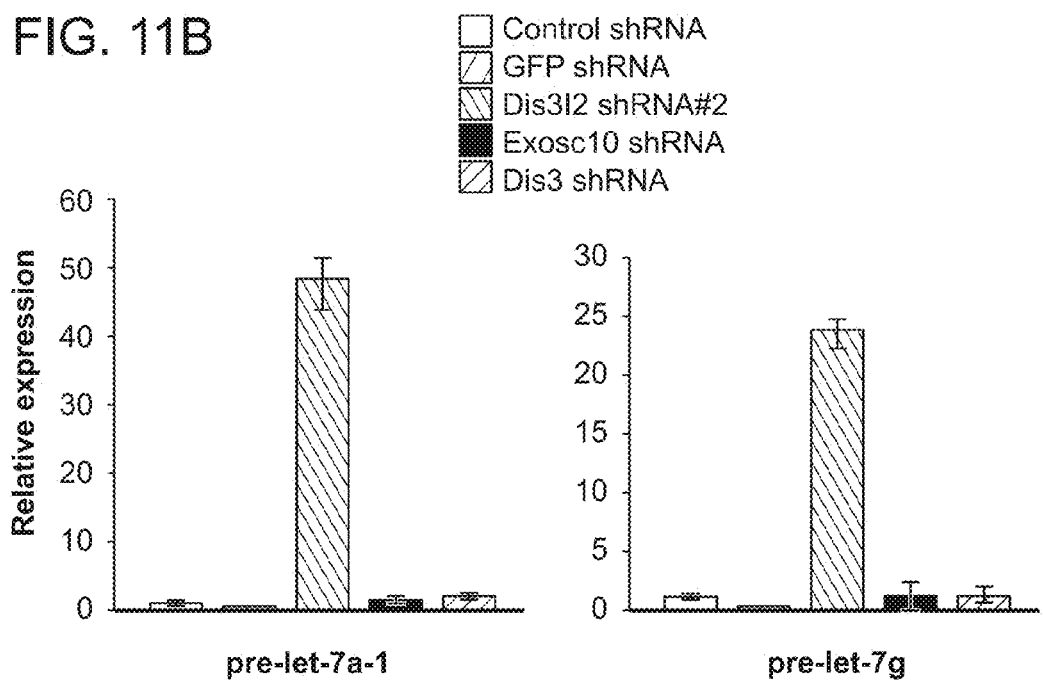
Figure 12A:
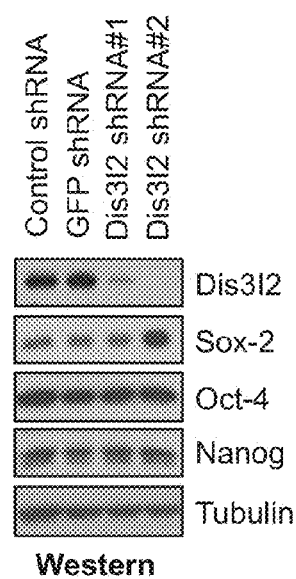
FIG. 12. Dis3l2-depleted embryonic stem cells display elevated expression of pluripotency genes and delayed differentiation. (a) Whole-cell extracts from V6.5 ESCs expressing shRNA against control, GFP, or Dis3l2 were examined by Western blotting for expression of the indicated proteins. (b) V6.5 ESCs expressing control or Dis3l2 shRNA were differentiated by removing LIF. Cells were collected at the indicated time points. Whole-cell extracts were examined by Western blotting for the expression of Dis3l2 and the pluripotency factors. (c) As in (b) except a different shRNA (shRNA#1) was used in an independent experiment. (d) q.RT-PCR analysis of the RNA extracted from the same cells analyzed in (a). Error bars±S.D. (n=3).
Figure 12C:
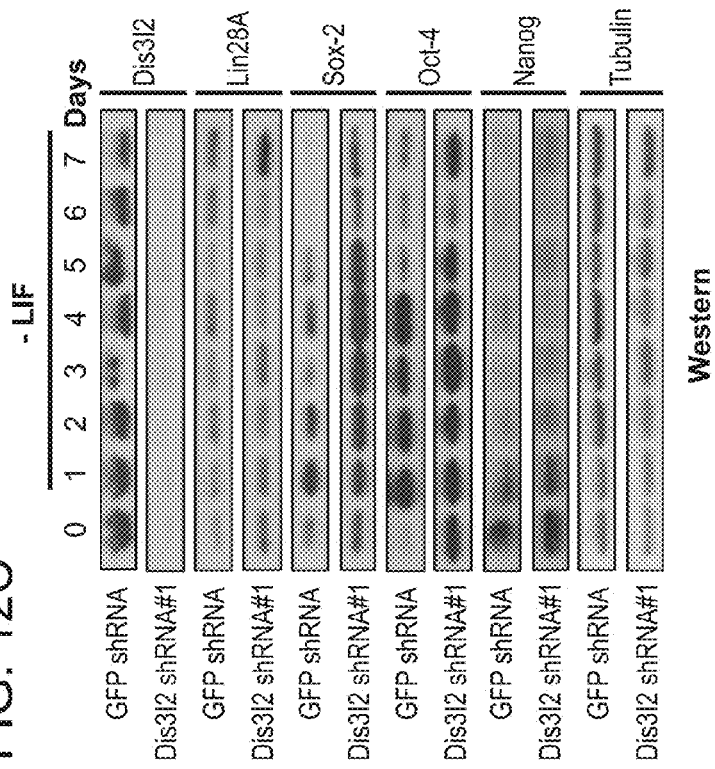
Figure 12B:
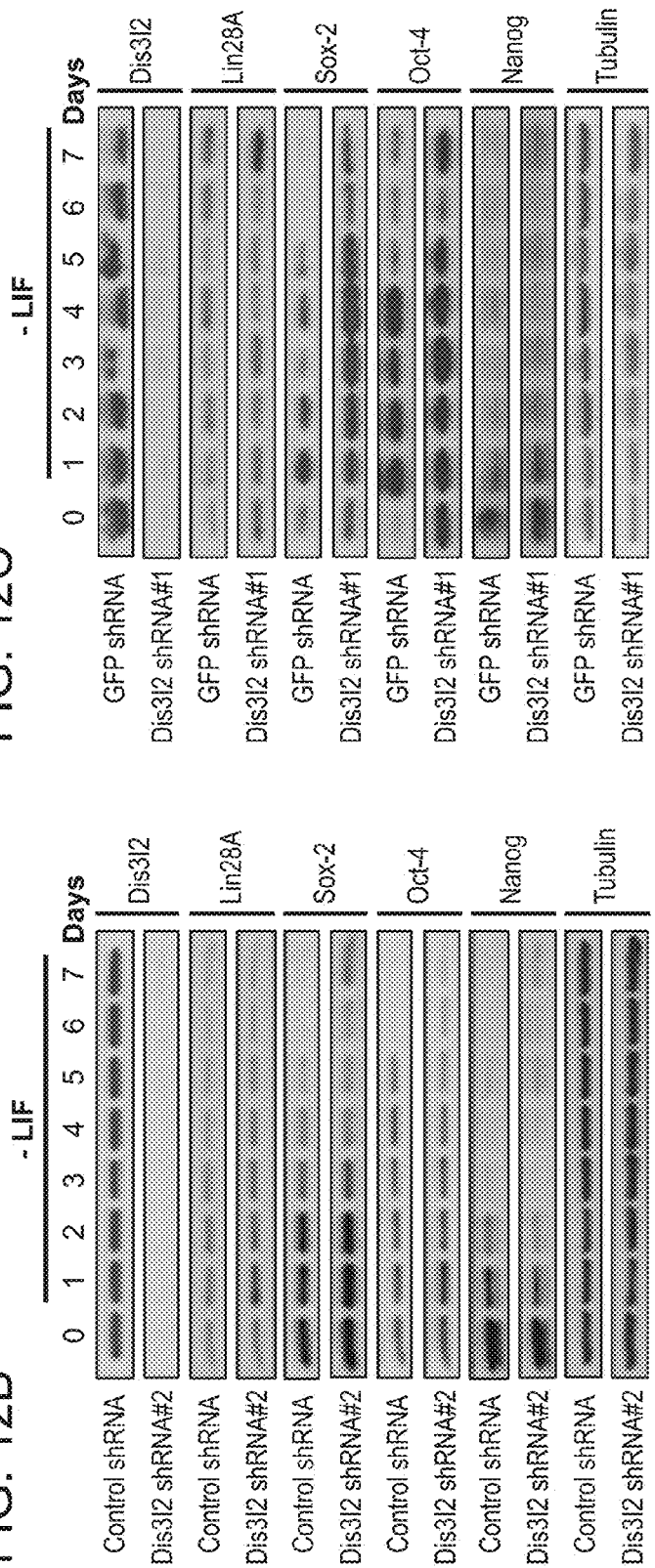
Figure 12D:
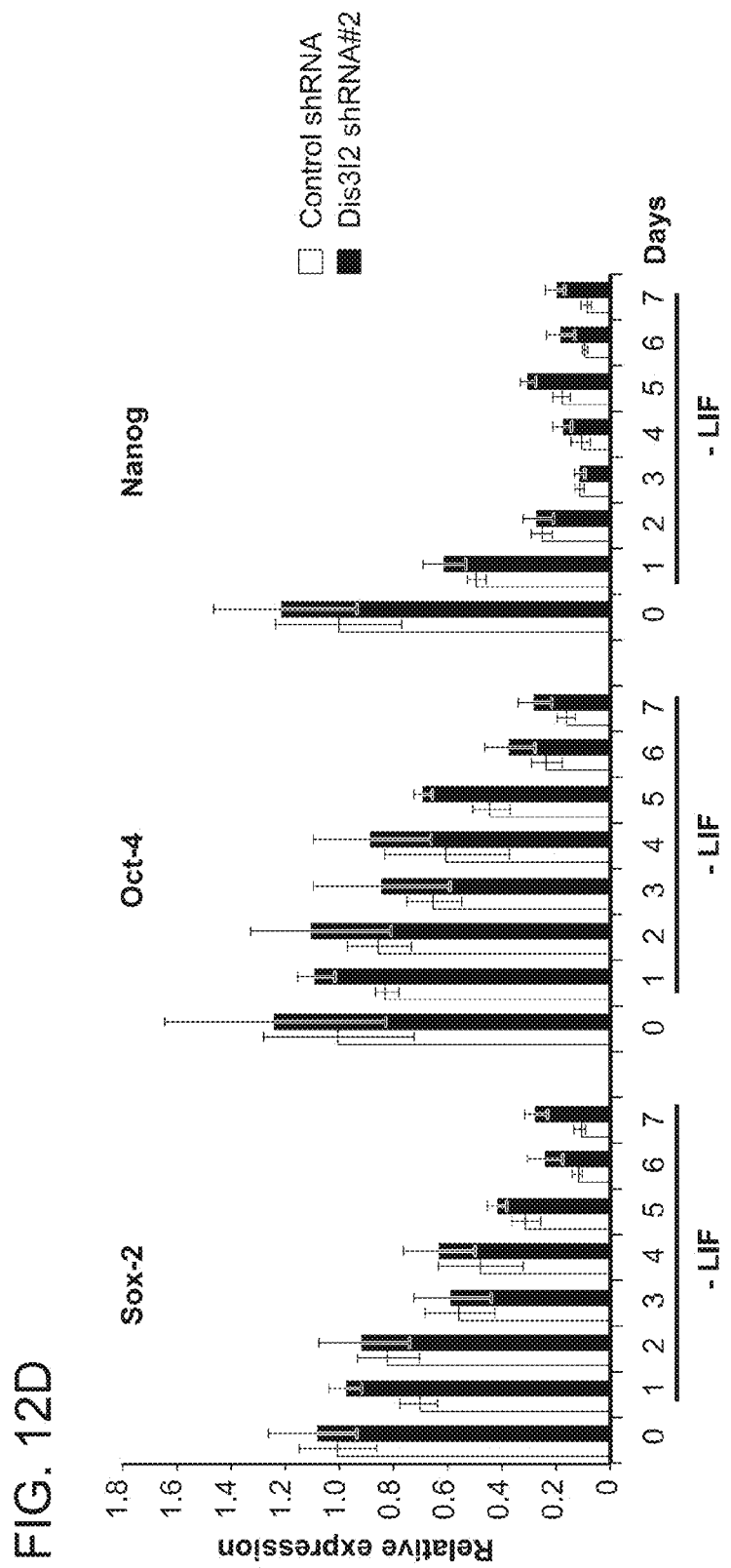

To confirm these observations and to further explore the relevance of Dis3l2 in ESCs, Applicant generated stable Dis3l2 knockdown cells lines using two different shRNAs (FIG. 10a). Levels of mature let-7 were unaffected by Dis3l2-depletion (FIG. 10b). However, there was a dramatic accumulation of uridylated pre-let-7 RNAs in these samples (FIG. 10c). Levels of pri-let-7 were again unaffected by Dis3l2 knockdown (FIG. 10d). The amount of uridylated pre-let-7 detected correlated with the extent of Dis3L2 depletion and, therefore, the most effective shRNA (shRNA#2) was selected for further analyses. Applicant used mixtures of synthetic uridylated pre-let-7a-1 and uridylated pre-let-7g to further validate the specificity of this q.RT-PCR-based assay and were able to demonstrate that the relative amounts of these pre-miRNAs was within the linear range of the assay (FIG. 10). To further confirm the direct role of Dis3l2 in the regulation of uridylated pre-let-7 levels Applicant performed cDNA rescue experiments in which the Dis3l2 knockdown ESC line was transfected with either wild-type or mutant Dis3l2-expressing plasmids. Analysis of RNA from these cells by Northern blot as well as q.RT-PCR revealed that the high levels of uridylated pre-let-7 RNA that accumulated in Dis3l2-knockdown cells could be substantially rescued by reintroduction of wild-type but not the catalytically inactive Dis3l2 (FIGS. 4*h-j*). Furthermore, levels of uridylated pre-let-7 were not further increased by the simultaneous knockdown of Dis3l1 and Dis3l2, thereby providing further evidence that these related cytoplasmic nucleases are not functionally redundant in ESCs (FIGS. 4*h-j* and FIGS. 10*f* and 10*g*). Finally Applicant individually depleted two additional 3'-5' exonucleases, Exosc10 (also known as mammalian RRP6) and Rrp44 (also known as mammalian Dis3) from ESCs and measured relative pre-let-7 levels by q.RT-PCR. In contrast to the strong accumulation of uridylated pre-let-7 in Dis3l2-depleted cells, knockdown of these exosome-associated nucleases did not have any effect on uridylated pre-let-7 levels (FIG. 11). These results provide strong support that Dis3l2 is the downstream nuclease that mediates the decay of uridylated pre-let-7 in the Lin28 pathway.

Example 2: Assessment of Results of Dis3l2 Depletion in Embryonic Stem Cells

Figure 13:
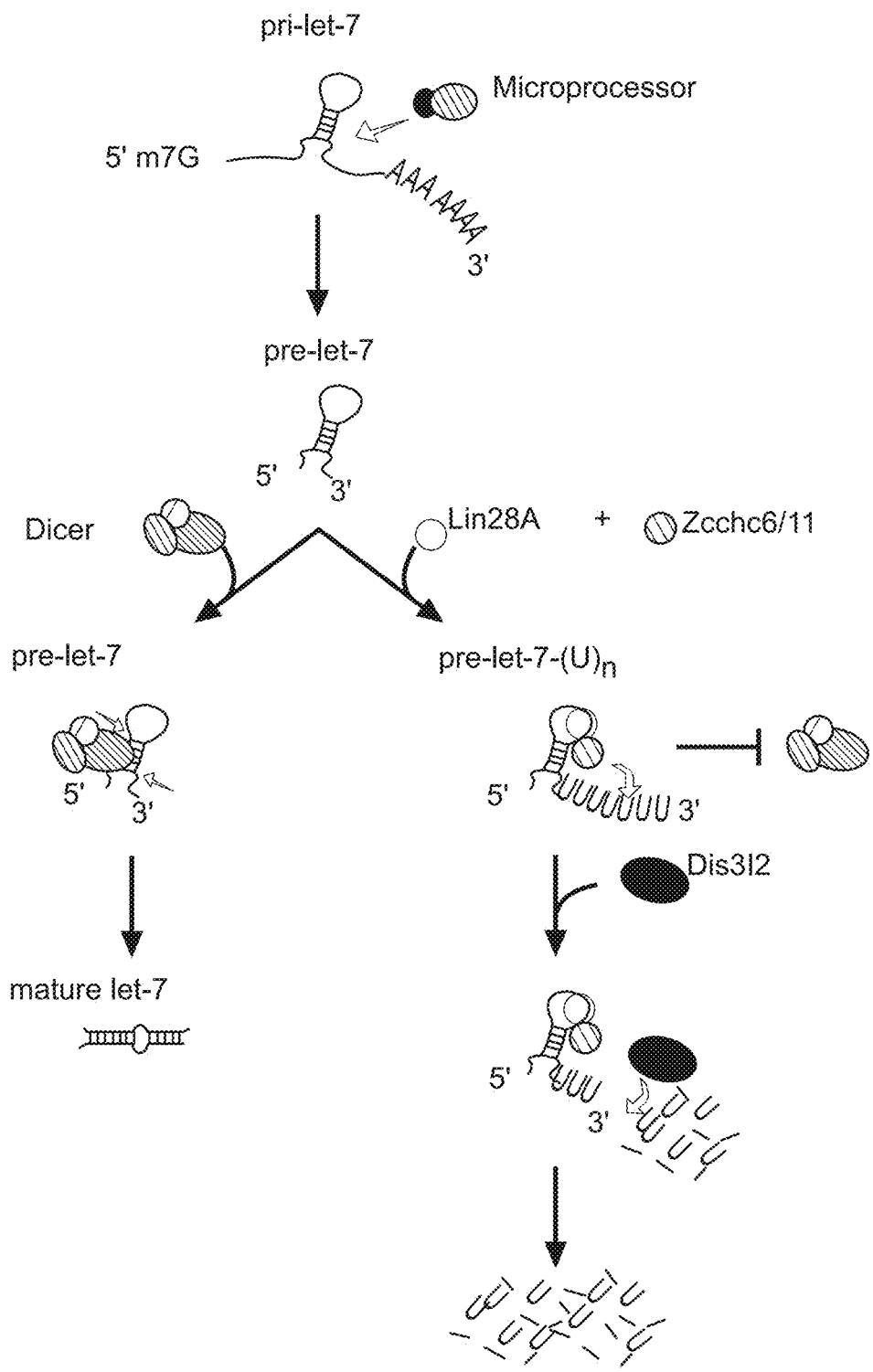
FIG. 13. Model for the role of Dis3l2 in the Lin28-let-7 pathway. After being transcribed by RNA polymerase II, pri-let-7 is processed by the Microprocessor complex of Drosha and DGCR8 in the nucleus to yield pre-let-7. Pre-let-7 is then exported to the cytoplasm, and, in the absence of Lin28A, further processed by Dicer to produce mature let-7 duplex. However, pre-let-7 may also interact with Lin28A through its terminal loop, which impedes Dicer cleavage by recruiting Zcchc11 and Zcchc6 to induce pre-let-7 uridylation. Uridylated pre-let-7 is recognized by the 3'-5' exonuclease Dis3l2 that ultimately leads to its destruction to prevent let-7 expression in embryonic cells.

As described further herein, Dis3l2 display elevated expression of pluripotency genes and delayed differentiation. The data identify Dis3l2 as a new component of the Lin28-let-7 regulatory pathway as the downstream nuclease response for the decay of uridylated pre-let-7 (FIG. 13). Since the Lin28-let-7 axis is central to coordinating ESC self-renewal and pluripotency Applicant was motivated to examine consequences of Dis3l2-depletion in this context. They observed elevated expression of Sox2 in the stable knockdown cells that were most depleted for Dis3l2, suggesting that Dis3l2 levels may impact ESC pluripotency (FIG. 6*a*). To further test this, Applicant examined the kinetics of ESC monolayer differentiation over a time-course of several days after the removal of leukemia inhibitory factor (LIF) from the culture media. As revealed by Western blot, Applicant found that Dis3l2-deficient ESCs displayed compromised differentiation compared to control ESCs with persistent expression of pluripotency genes including Nanog, Oct4, and Sox2 (FIG. 6). These results support a role for Dis3l2 in regulating pluripotency by facilitating the switch from ESC self-renewal to the cell differentiation program.

Experimental Procedures
Methods and materials used in the work described herein.
Cell Culture and Cell Lines.

HEK293 cells were maintained in DMEM, P19 cells in MEMα+GlutaMax™-1, and ESCs in DMEM with ESGRO (1,000 units/ml), supplemented with antibiotics, and 10% (for HEK293, P19) or 15% (for ESC) fetal bovine serum. Dox-inducible Flag-Lin28A ESC line was generated as described (Hagan et al., 2009). The MISSION® shRNA plasmid DNA (Sigma, TRC number TRCN0000120760 for shRNA#1 and TRCN0000120761 for shRNA#2) together with pLP1, pLP2, and VSVG were transfected into 293T cells to produce lentiviral particles that were used to infect V6.5 ESCs. The Dis3l2 shRNA stable cell lines were then created by puromycin (2.5 μg/ml) selection.

Affinity Pull-Down Assays.

For RNA affinity pull-down, synthetic mmu-pre-let-7a-1 or mmu-pre-let-7a-1+14U was conjugated to adipic acid dihydrazide agarose beads and incubated with whole-cell extract from P19 cells (Viswanathan et al., 2008). The affinity eluate was subjected to SDS-polyacrylamide gel electrophoresis (SDS-PAGE) followed by Coomassie blue staining Bands were excised, and subjected to mass spectroscopic sequencing. The sequencing results were further confirmed by Western blotting. For affinity purification of Flag-Lin28A, KH2 ESCs were treated with Dox at 6 μg/ml for 48 hours and then harvested in the lysis buffer (20 mM Tris-HCl, pH 8.0, 137 mM NaCl, 1 mM EDTA, 1% (v/v) Triton X-100, 10% (v/v) Glycerol, 1.5 mM $MgCl_2$, 1 mM DTT, 0.2 mM PMSF) supplemented with 40 units/ml of RNase inhibitor (rRNasin, Promega). Protein complexes were affinity-purified using α-Flag M2 agarose beads (Sigma). Beads were extensively washed with lysis buffer for a total of seven times before elution with 0.5 mg/ml Flag peptide. The eluates were analyzed by SDS-PAGE and Western blotting.

Plasmids and DNA Cloning.
Dis3l2 cDNA was generated by PCR using the forward
(SEQ ID NO: 1)
(5'-aagctt<u>gcggccgcg</u>AACCATCCTGACTACAAGCTGAACCTTCGG-3')

and the reverse
(SEQ ID NO: 2)
(5'-agaccta<u>gtcgac</u>TCAGTCCTCAGGCTCCTCATCAGACGCC-3')

primers, and was cloned into the NotI and SalI sites of pFlag-CMV2 (Sigma). For generating Dis3l2 D389N mutant, site-directed mutagenesis was performed using the forward (5'-CTGCTCGCGACCTTAATGATGCCCTCGC-3') (SEQ ID NO:3) and the reverse (5'-GCGAGGGCATCATTAAGGTCGCGAGCAG-3') (SEQ ID NO:4) primers. For generating His-tagged Dis3l2, PCR product from the forward
(SEQ ID NO: 5)
(5'-actag<u>gaattcg</u>AACCATCCTGACTACAAGCTGAACCTTCGG-3')

and the reverse
(SEQ ID NO: 6)
(5'-aagctt<u>gcggccgc</u>TCAGTCCTCAGGCTCCTCATCAGACGCC-3')

primers was cloned into the EcoRI and NotI sites of pET-Duet-1. For CT-GFP and NT-GFP fusions, the GFP Fusion TOPO TA expression kits (Invitrogen) were used. For CT-GFP fusions, the forward (5'-ACC ATG AAC CAT CCT GAC TAC AAG CTG AAC-3') (SEQ ID NO:7) and the reverse (5'-CGT CCT CAG GCT CCT CAT CAG-3') (SEQ ID NO:8) primers were used. For NT-GFP fusions, the forward (5'-AAC CAT CCT GAC TAC AAG CTG AAC-3') (SEQ ID NO:9) and the reverse (5'-TCA GTC CTC AGG CTC CTC ATC AG-3') (SEQ ID NO:10) primers were used. For deletion mutants, Dis3l2 truncated cDNA were amplified by PCR with the forward (5'-AAC AAG CGG CCG CGA ACC ATC CTG ACT ACA AGC TGA ACC-3') (SEQ ID NO:11) and the reverse (5'-AAC AAG AAT TGA GTA GCC CAG AGC AGC AGC-3') (SEQ ID NO:12) primers to generate the C-terminus deletion mutant, with the forward (5'-AAC AAG CGG CCG CGA GAA GAG ACC TAA GGA AAG ACT GTA TCT TCA C-3') (SEQ ID NO:13) and the reverse (5'-AAC AAG AAT TCA GTC CTC AGG CTC CTC ATC-3') (SEQ ID NO:14) primers to generate the N-terminus deletion and with the forward (5'-AAC AAG CGG CCG CGA GAA GAG ACC TAA GGA AAG ACT GTA TCT TCA C-3') (SEQ ID NO:15) and the reverse (5'-AAC AAG AAT TGA GTA GCC CAG AGC AGC AGC-3') (SEQ ID NO:16) primers to generate the N and C-terminus deletion. These PCR products were cloned into NotI and EcoRI sites of pFLAG-CMV2 vector (Sigma).

Recombinant Dis3l2 Protein Purification

Transformed BL21-CodonPlus® Competent bacteria (Stratagene) were grown to an OD600 nm of 0.4-0.6. Expression was induced 100 µM IPTG for 2-3 hours. Cell pellets were resuspended in cold lysis buffer [20 mM imidazole pH 8.0 in PBS, 0.1% Phenylmethyl sulfonyl fluoride (PMSF)] and sonicated. Cleared lysates were incubated with Ni-NTA beads and after 90 minutes incubation at 4° C. the beads were washed with 80 column volumes wash buffer [10 mM Tris (pH 7.8), 50 mM imidazole pH 8.0, 500 mM NaCl, 0.1% PMSF). Bound His-tagged proteins were eluted from the column with 1 volume elution buffer [10 mM Tris (pH 7.8), 500 mM imidazole pH 8.0, 500 mM NaCl, 0.1% fresh PMSF] and dialyzed overnight against BC100 [20 mM Tris-HCl (pH 7.8), 100 mM KCl, 0.2 mM EDTA, 10% glycerol]. Purified protein was dialyzed against RNA degradation buffer (see below) and supplemented with 20% glycerol before storage at –80° C. For affinity purification of ectopically expressed FLAG-Lin28A or FLAG-Lin28A W46A, V6.5 ESC were transfected using Lipofectamine 2000 (Invitrogen) and collected 48 hours later. Cells were lysed as described above, except for the addition of RNase A (20 mg/ml final, QIAGEN) where indicated.

RNA Degradation Assays

RNA degradation assays were performed in a total of 20 µl reaction using 6.25 nM 5' end-labeled pre-miR-21, pre-let-7a-1, or pre-let-7a-1+14U RNA (see Table 2) together with Dis3l2 and/or Lin28A. The reactions were set up in the RNA degradation buffer (20 mM HEPES-KOH pH 7.5, 50 mM KCl, 0.05 mM MgCl2, 1 mM DTT) and incubated at 37° C. for 90 minutes. For time-course assays; recombinant 6x-His Dis3l2 was incubated with radiolabeled pre-let-7a-1 or pre-let-7a-1+14U. Bands from three independent experiments were quantified using ImageJ (NIH) and plotted using Prism (Graphpad). Values were fitted to one-phase decay curves with error bars representing +/- s.d. (n=3). For Uridylation-stimulated degradation assays; in vitro uridylation assays were performed as described previously[20,26,27] except with the addition of 10 µM cold competitor uridine triphosphate and immunopurified Dis3l2 where indicated.

In vitro Transcription of Pre-miRNAs

In vitro transcribed pre-let-7 RNAs were generated as substrates RNA degradation assays (in FIG. 3b). DNA templates for in vitro transcription of pre-let-7 with different 3' ends by PCR amplification using were generated using a universal (SEQ ID NO: 17)
5'-primer (acggttcagc<u>TAATACGACTCACTATAGGG</u>TGAGGTAG

TAGTTTGTACAGTTTGAGG)

promoter sequence underlined) and a 3'-primer listed in the Table 1 to amplify from a plasmid DNA template containing pri-let-7[10]. PCR products were cloned and sequence verified. DNA templates (PCR products) were gel-purified and in vitro transcription was performed according to Riboprobe in-vitro transcription systems using a-32P rGTP and T7 RNA polymerase (Promega). The labeled pre-miRNAs were treated with RQ1 DNase and cleaned by illustra MicroSpin G-25 Column (GE Healthcare Life Sciences).

TABLE 1

| pre-let-7g-(U, C, or A)$_n$ | 3'-primer |
|---|---|
| pre-let-7g-0U | GCAAGGCAGTGGCCTGTACAGTTATC (SEQ ID NO: 18) |
| pre-let-7g-1U | aGCAAGGCAGTGGCCTGTACAGTTAT C (SEQ ID NO: 19) |
| pre-let-7g-3U | aaaGCAAGGCAGTGGCCTGTACAGTT ATC (SEQ ID NO: 20) |
| pre-let-7g-5U | aaaaaGCAAGGCAGTGGCCTGTACAG TTATC (SEQ ID NO: 21) |
| pre-let-7g-10U | aaaaaaaaaaGCAAGGCAGTGGCCTG TACAGTTATC (SEQ ID NO: 22) |
| pre-let-7g-14U | aaaaaaaaaaaaaaGCAAGGCAGTGG CCTGTACAGTTATC (SEQ ID NO: 23) |
| pre-let-7g-20U | aaaaaaaaaaaaaaaaaaaaGCAAGG CAGTGGCCTGTACAGTTATC (SEQ ID NO: 24) |
| pre-let-7g-14A | ttttttttttttttGCAAGGCAGTGG CCTGTACAGTTATC (SEQ ID NO: 25) |
| pre-let-7g-14C | ggggggggggggggGCAAGGCAGTGG CCTGTACAGTTATC (SEQ ID NO: 26) |

RNA Electromobility Shift Assays (EMSA)

EMSA experiments were performed as described previously[20]. Briefly, 1 nM of the indicated radiolabeled synthetic RNA was incubated in the binding buffer (50 mM Tris pH 7.6, 100 mM NaCl, 10 mM µ-Mercaptoethanol, 1 unit/µl RNaseOUT) with varying concentrations of catalytically inert recombinant 6x-His Dis3L2 or recombinant 6x-His Lin28 in the absence of competitor RNA. Nucleoprotein complexes were resolved by 4-20% non-denaturing TBE gel electrophoresis (Biorad, #345-0059) and visualized by autoradiography.

Antibodies and Synthetic RNA

TABLE 2

Antibodies and the working concentrations

| Antibody | Cat. # | Source | Conc. used |
|---|---|---|---|
| α-Dis3l2 | NBP1-84740 | Novus Biologicals | 0.4 µg/ml |
| α-Zcchc11 | 18980-1-AP | ProteinTech Group | 1:1,000 |
| α-Zcchc6 | Custom-made | Open Biosystems | 1:500 |
| α-Dis3 | Cat #14689-1-AP | ProteinTech Group | 1:1000 |
| α-Exosc10 | Cat # ab50558 | Abcam | 1 µg/ml |
| α-Lin28A (A177) | #3978 | Cell Signaling | 1:1,000 |
| α-Sox2 | ab97959 | Abcam | 1 µg/ml |
| α-Oct4 | ab19857 | Abcam | 0.2 µg/ml |
| α-Nanog | ab70482 | Abcam | 0.4 µg/ml |
| α-Tubulin | ab6046 | Abcam | 1:10,000 |
| α-Flag | A8592 | Sigma | 1:5,000 |

Transfections and siRNA/shRNA Knockdowns

All transfections were performed with Lipofectamine (Invitrogen) per manufacturer's instructions. The sequences of the shRNA hairpins and siRNAs are listed in Table 3. Lentivirus production, infection, and stable cell selection are as described[22].

TABLE 3

The synthetic RNA sequences

| RNA | Cat. # | Source | Sequence |
|---|---|---|---|
| mmu-pre-let-7a-1 | N/A | Dharmacon | UGAGGUAGUAGGUUGU AUAGUUUUAGGGUCAC ACCCACCACUGGGAGA UAACUAUACAAUCUAC UGUCUUUCC (SEQ ID NO: 27) |
| mmu-pre-let-7a-1 + 14U | N/A | Dharmacon | UGAGGUAGUAGGUUGU AUAGUUUUAGGGUCAC ACCCACCACUGGGAGA UAACUAUACAAUCUAC UGUCUUUCCUUUUUU (SEQ ID NO: 28) |
| mmu-pre-miR-21 | N/A | Dharmacon | UAGCUUAUCAGACUGA UGUUGACUGUUGAAUC UCAUGGCAACAGCAGU CGAUGGGCUGUC (SEQ ID NO: 29) |
| control siRNA #1 | D-001810-01 | Dharmacon | UGGUUUACAUGUCGAC UAA (SEQ ID NO: 30) |
| control siRNA #2 | D-001810-02 | Dharmacon | UGGUUUACAUGUUGUG UGA (SEQ ID NO: 31) |
| Lin28A siRNA | Custom | Dharmacon | GGGUUGUGAUGACAGG CAA (SEQ ID NO: 32) |
| Zcchc11 siRNA | J-065226-06 | Dharmacon | GGGCUAAGCUGUGCUA UAU (SEQ ID NO: 33) |
| mouse Dis312 siRNA#1 | J-054755-10 | Dharmacon | CCGCUUUGCUGACGUC AUA (SEQ ID NO: 34) |
| mouse Dis312 siRNA#2 | J-054755-11 | Dharmacon | GAAUUUACGUACCUCU CAA (SEQ ID NO: 35) |
| mouse Dis311 siRNA#1 | J-054584-10 | Dharmacon | AGGAACUACUGGACGG AAA (SEQ ID NO: 36) |
| mouse Dis311 siRNA#2 | J-054584-11 | Dharmacon | UGAAACAGAAGGCGUA UUU (SEQ ID NO: 37) | mRNA and miRNA Quantitative RT-PCR

Total RNA was isolated using TRIzol reagent (Invitrogen). For fractionation of less than 200 nucleotides (nt) long RNA, total RNA was processed by mirVana™ miRNA Isolation Kit according to the manufacturer's instructions (Cat #AM1560, Ambion). For mRNA, 100 ng of total RNA was reverse transcribed using random hexamers and SuperScript III (Invitrogen). For mature miRNA, 10 ng of total RNA was reverse transcribed using gene-specific stem-loop RT primers and Multiscribe reverse transcriptase (Applied Biosystems). For pre-miRNA, 1 µg of less than 200 nt fractionated RNA was first treated with 0.66 unit of RNase-free DNase (Promega) (60 min at 37° C.), stopped with 1 mM of EDTA (10 min at 65° C.), and reverse transcribed by oligo(dA)$_{12}$ (60 min at 50° C.) using SuperScript III (Invitrogen). The resulting cDNA was further digested with RNase H (30 min at 37° C.). For mRNA and pre-miRNA, iQ SYBR Green Supermix (Bio-Rad) was used for quantitating the cDNA. For mature-miRNA, TaqMan Universal PCR Master Mix, No AmpErase UNG (Applied Biosystems) was used for cDNA detection. All quantitative PCR were performed using iCycler iQ Multicolor Real-Time PCR Detection System (Bio-Rad). Normalization controls include ACTB for mRNAs as well as for pri-miRNAs, U6 for pre-miRNA, and snoRNA142 for mature miRNAs. For all RT-PCRs, minus reverse transcriptase (-RT) and water control samples were included and in all cases the signals were undetectable (data not shown). The primer sequences used in this study are listed in Table 4.

TABLE 4

Primer sequences used in quantitative PCR

| Target gene | Forward sequence | Reverse sequence |
|---|---|---|
| pre-let-7a-1 | TGAGGTAGTAGGTTGT ATAGTTTTAGGG (SEQ ID NO: 38) | GGAAAGACAGTAGATTGTAT AGTTATC (SEQ ID NO: 48) |
| pri-let-7a-1 | CTTTCAACATTCACC CTGGATGTTC (SEQ ID NO: 39) | GAGACCCCATGAATGCAGACT TT (SEQ ID NO: 49) |
| pre-let-7g | TGAGGTAGTAGTTTG TACAGTTTGAGG (SEQ ID NO: 40) | GCAAGGCAGTGGCCTGTACAG TTATC (SEQ ID NO: 50) |
| pri-let-7g | GTTCTCTTTTGCCTG ATTCCAGG (SEQ ID NO: 41) | CATTTGGTAGCTGGTGCACTG (SEQ ID NO: 51) |
| U6 | CTCGCTTCGGCAGCA CA (SEQ ID NO: 42) | AACGCTTCACGAATTTGCGT (SEQ ID NO: 52) |
| ACTB | CAGAAGGAGATTACT GCTCTGGCT (SEQ ID NO: 43) | TACTCCTGCTTGCTGATCCAC ATC (SEQ ID NO: 53) |
| Dis311 | AGTTGACAGACATAG CTCGCCACA (SEQ ID NO: 44) | TGGTTGGCTAGGATCATGCAC TCA (SEQ ID NO: 54) |
| Oct-4 | AAAGCAACTCAGAGG GAACCTCCT (SEQ ID NO: 45) | TAGCTCCTTCTGCAGGGCTTT CAT (SEQ ID NO: 55) |
| Nanog | TGGTGTCTTGCTCTT TCTGTGGGA (SEQ ID NO: 46) | ACACTCATGTCAGTGTGATGG CGA (SEQ ID NO: 56) |
| Sox-2 | GAGGAAAGGGTTCTT GCTGGGTTT (SEQ ID NO: 47) | AACGGTCTTGCCAGTACTTGC TCT (SEQ ID NO: 57) |

Northern Blotting

10 µg total RNA from each sample was used for Northern blotting as previously described[40]. Probe sequences for detecting precursor and mature miRNA are as follows: 5'-TATCTCCTGTACCGGGTGGTATCATAGACCCTCA-3' (SEQ ID NO:58) for pre-let-7g; 5'-AACTATACAAC-CTACTACCTCA-3' (SEQ ID NO:59) for let-7a; 5'-AACT-GTACAAACTACTACCTCA-3' (SEQ ID NO:60) for let-7g.

Dicer Assays

Recombinant Flag-Dicer Protein was purified from insect cells as previously described[40]. Dicer processing of pre-let-7 or pre-let-7+14U was performed by incubating recombinant Dicer with gel-purified 5'-end labeled synthetic pre-miRNA in a buffer containing 3.2 mM MgCl2, 20 mMTris-HCl (pH 7.9), 0.1M KCl, 10% glycerol, 5 mM DTT, 0.2 mM PMSF, 40 units/ml of RNase inhibitor (RNasin, Promega) for 1 h at 37° C. Samples were resolved by 15% denaturing polyacrylamide gel.

Supplementary Methods

Fluorescence Microscopy

V6.5 ESC were grown on gelatinized coverslips for 24 hours, before fixing with 4% paraformaldehyde for 20 minutes at room temperature. For indirect immunofluorescence, cells were permeabilized with 0.2% Triton X-100 for 5 minutes at room temperature and then blocked in PBS supplemented with 5% FBS for 30 minutes. Cells were incubated at 4° C. overnight with primary antibodies at 1:500 dilution. The next day, cells were washed with PBS supplemented with 5% FBS and incubated with the secondary antibodies at 1:400 dilution for 1 hour (Invitrogen, anti-mouse A11005, anti-Rabbit A21206) in the dark at room temperature. The coverslips were mounted with Vectashield mounting solution with DAPI (VectorLabs). For fluorescence microscopy experiments, cells were transfected with GFP-fusion constructs and after 24 hours fixed as described above. Cells were washed with PBS three times and coverslips were mounted as described above.

RT-PCR Analysis of Dis3l2 Transcript Variants

Total RNA from V6.5 ESC was reverse transcribed using either random hexamers or oligo-dT and SuperScript III according to manufacturer's protocol (Invitrogen). PCR analysis was performed using the forward (5'-TGT CCA AGG AGG ATG TTT CAG-3') (SEQ ID NO:61) and the reverse (5'-CAG GGA TGT CAG CTT CAT AAG T-3') (SEQ ID NO:62) primers. pFLAG-CMV2 Dis3l2.2 (referred to as Dis3l2) was used as a positive control.

REFERENCES

Ambros, V., and Horvitz, H. R. (1984). Heterochronic mutants of the nematode Caenorhabditis elegans. Science 226, 409-416.

Astuti, D., Morris, M. R., Cooper, W. N., Staals, R. H., Wake, N. C., Fews, G. A., Gill, H., Gentle, D., Shuib, S., Ricketts, C. J., et al. (2012). Germline mutations in DIS3L2 cause the Perlman syndrome of overgrowth and Wilms tumor susceptibility. Nat Genet 44, 277-284.

Blum, E., Carpousis, A. J., and Higgins, C. F. (1999). Polyadenylation promotes degradation of 3'-structured RNA by the Escherichia coli mRNA degradosome in vitro. J Biol Chem 274, 4009-4016.

Carpousis, A. J., Vanzo, N. F., and Raynal, L. C. (1999). mRNA degradation. A tale of poly(A) and multiprotein machines. Trends Genet 15, 24-28.

Chang, H. M., Martinez, N. J., Thornton, J. E., Hagan, J. P., Nguyen, K. D., and Gregory, R. I. (2012). Trim71 cooperates with microRNAs to repress Cdkn1a expression and promote embryonic stem cell proliferation. Nat Commun 3, 923.

Chang, T. C., Zeitels, L. R., Hwang, H. W., Chivukula, R. R., Wentzel, E. A., Dews, M., Jung, J., Gao, P., Dang, C. V., Beer, M. A., et al. (2009). Lin-28B transactivation is necessary for Myc-mediated let-7 repression and proliferation. Proc Natl Acad Sci U.S.A. 106, 3384-3389.

Chendrimada, T. P., Gregory, R. I., Kumaraswamy, E., Norman, J., Cooch, N., Nishikura, K., and Shiekhattar, R. (2005). TRBP recruits the Dicer complex to Ago2 for microRNA processing and gene silencing. Nature 436, 740-744.

Dangi-Garimella, S., Yun, J., Eves, E. M., Newman, M., Erkeland, S. J., Hammond, S. M., Minn, A. J., and Rosner, M. R. (2009). Raf kinase inhibitory protein suppresses a metastasis signalling cascade involving LIN28 and let-7. EMBO J 28, 347-358.

Denli, A. M., Tops, B. B., Plasterk, R. H., Ketting, R. F., and Hannon, G. J. (2004). Processing of primary microRNAs by the Microprocessor complex. Nature 432, 231-235.

Diskin, S. J., Capasso, M., Schnepp, R. W., Cole, K. A., Attiyeh, E. F., Hou, C., Diamond, M., Carpenter, E. L., Winter, C., Lee, H., et al. (2012). Common variation at 6q16 within HACE1 and LIN28B influences susceptibility to neuroblastoma. Nat Genet 44, 1126-1130.

Ebert, M. S., and Sharp, P. A. (2012). Roles for microRNAs in conferring robustness to biological processes. Cell 149, 515-524.

Fabian, M. R., Sonenberg, N., and Filipowicz, W. (2010). Regulation of mRNA translation and stability by microRNAs. Annu Rev Biochem 79, 351-379.

Frost, R. J., and Olson, E. N. (2011). Control of glucose homeostasis and insulin sensitivity by the Let-7 family of microRNAs. Proc Natl Acad Sci USA.

Gregory, R. I., Yan, K. P., Amuthan, G., Chendrimada, T., Doratotaj, B., Cooch, N., and Shiekhattar, R. (2004). The Microprocessor complex mediates the genesis of microRNAs. Nature 432, 235-240.

Hagan, J. P., Piskounova, E., and Gregory, R. I. (2009). Lin28 recruits the TUTase Zcchc11 to inhibit let-7 maturation in mouse embryonic stem cells. Nat Struct Mol Biol 16, 1021-1025.

Heo, I., Joo, C., Cho, J., Ha, M., Han, J., and Kim, V. N. (2008). Lin28 mediates the terminal uridylation of let-7 precursor MicroRNA. Mol Cell 32, 276-284.

Heo, I., Joo, C., Kim, Y. K., Ha, M., Yoon, M. J., Cho, J., Yeom, K. H., Han, J., and Kim, V. N. (2009). TUT4 in concert with Lin28 suppresses microRNA biogenesis through pre-microRNA uridylation. Cell 138, 696-708.

Hutvagner, G., McLachlan, J., Pasquinelli, A. E., Balint, E., Tuschl, T., and Zamore, P. D. (2001). A cellular function for the RNA-interference enzyme Dicer in the maturation of the let-7 small temporal RNA. Science 293, 834-838.

Iliopoulos, D., Hirsch, H. A., and Struhl, K. (2009). An epigenetic switch involving NF-kappaB, Lin28, Let-7 MicroRNA, and IL6 links inflammation to cell transformation. Cell 139, 693-706.

Iorio, M. V., and Croce, C. M. (2012). MicroRNA dysregulation in cancer: diagnostics, monitoring and therapeutics. A comprehensive review. EMBO Mol Med 4, 143-159.

Ketting, R. F. (2011). The many faces of RNAi. Dev Cell 20, 148-161.

LaCava, J., Houseley, J., Saveanu, C., Petfalski, E., Thompson, E., Jacquier, A., and Tollervey, D. (2005). RNA degradation by the exosome is promoted by a nuclear polyadenylation complex. Cell 121, 713-724.

Melton, C., Judson, R. L., and Blelloch, R. (2010). Opposing microRNA families regulate self-renewal in mouse embryonic stem cells. Nature 463, 621-626.

Mendell, J. T., and Olson, E. N. (2012). MicroRNAs in stress signaling and human disease. Cell 148, 1172-1187.

Mondol, V., and Pasquinelli, A. E. (2012). Let's make it happen: the role of let-7 microRNA in development. Curr Top Dev Biol 99, 1-30.

Mullen, T. E., and Marzluff, W. F. (2008). Degradation of histone mRNA requires oligouridylation followed by decapping and simultaneous degradation of the mRNA both 5' to 3' and 3' to 5'. Genes Dev 22, 50-65.

Nam, Y., Chen, C., Gregory, R. I., Chou, J. J., and Sliz, P. (2011). Molecular Basis for Interaction of let-7 MicroRNAs with Lin28. Cell 147, 1080-1091.

Newman, M. A., Thomson, J. M., and Hammond, S. M. (2008). Lin-28 interaction with the Let-7 precursor loop mediates regulated microRNA processing. RNA 14, 1539-1549.

Norbury, C. J. (2010). 3' Uridylation and the regulation of RNA function in the cytoplasm. Biochem Soc Trans 38, 1150-1153.

Pasquinelli, A. E., Reinhart, B. J., Slack, F., Martindale, M. Q., Kuroda, M. I., Maller, B., Hayward, D. C., Ball, E. E., Degnan, B., Muller, P., et al. (2000). Conservation of the sequence and temporal expression of let-7 heterochronic regulatory RNA. Nature 408, 86-89.

Permuth-Wey, J., Kim, D., Tsai, Y. Y., Lin, H. Y., Chen, Y. A., Barnholtz-Sloan, J., Birrer, M. J., Bloom, G., Chanock, S. J., Chen, Z., et al. (2011). LIN28B polymorphisms influence susceptibility to epithelial ovarian cancer. Cancer Res 71, 3896-3903.

Piskounova, E., Polytarchou, C., Thornton, J. E., Lapierre, R. J., Pothoulakis, C., Hagan, J. P., Iliopoulos, D., and Gregory, R. I. (2011). Lin28A and Lin28B Inhibit let-7 MicroRNA Biogenesis by Distinct Mechanisms. Cell 147, 1066-1079.

Reinhart, B. J., Slack, F. J., Basson, M., Pasquinelli, A. E., Bettinger, J. C., Rougvie, A. E., Horvitz, H. R., and Ruvkun, G. (2000). The 21-nucleotide let-7 RNA regulates developmental timing in Caenorhabditis elegans. Nature 403, 901-906.

Rissland, O. S., and Norbury, C. J. (2009). Decapping is preceded by 3' uridylation in a novel pathway of bulk mRNA turnover. Nat Struct Mol Biol 16, 616-623.

Rottiers, V., and Naar, A. M. (2012). MicroRNAs in metabolism and metabolic disorders. Nat Rev Mol Cell Biol 13, 239-250.

Roush, S., and Slack, F. J. (2008). The let-7 family of microRNAs. Trends Cell Biol 18, 505-516.

Rybak, A., Fuchs, H., Smirnova, L., Brandt, C., Pohl, E. E., Nitsch, R., and Wulczyn, F. G. (2008). A feedback loop comprising lin-28 and let-7 controls pre-let-7 maturation during neural stem-cell commitment. Nat Cell Biol 10, 987-993.

Schmidt, M. J., West, S., and Norbury, C. J. (2011). The human cytoplasmic RNA terminal U-transferase ZCCHC11 targets histone mRNAs for degradation. RNA 17, 39-44.

Siomi, H., and Siomi, M. C. (2010). Posttranscriptional regulation of microRNA biogenesis in animals. Mol Cell 38, 323-332.

Staals, R. H., Bronkhorst, A. W., Schilders, G., Slomovic, S., Schuster, G., Heck, A. J., Raijmakers, R., and Pruijn, G. J. (2010). Dis3-like 1: a novel exoribonuclease associated with the human exosome. EMBO J 29, 2358-2367.

Thornton, J. E., Chang, H. M., Piskounova, E., and Gregory, R. I. (2012). Lin28-mediated control of let-7 microRNA expression by alternative TUTases Zcchc11 (TUT4) and Zcchc6 (TUT7). RNA 18, 1875-1885.

Thornton, J. E., and Gregory, R. I. (2012). How does Lin28 let-7 control development and disease? Trends Cell Biol 22, 474-482.

Tomecki, R., Kristiansen, M. S., Lykke-Andersen, S., Chlebowski, A., Larsen, K. M., Szczesny, R. J., Drazkowska, K., Pastula, A., Andersen, J. S., Stepien, P. P., et al. (2010). The human core exosome interacts with differentially localized processive RNases: hDIS3 and hDIS3L. EMBO J 29, 2342-2357. Viswanathan, S. R., and Daley, G. Q. (2010). Lin28: A microRNA regulator with a macro role. Cell 140, 445-449.

Viswanathan, S. R., Daley, G. Q., and Gregory, R. I. (2008). Selective blockade of microRNA processing by Lin28. Science 320, 97-100.

Viswanathan, S. R., Powers, J. T., Einhorn, W., Hoshida, Y., Ng, T. L., Toffanin, S., O'Sullivan, M., Lu, J., Phillips, L. A., Lockhart, V. L., et al. (2009). Lin28 promotes transformation and is associated with advanced human malignancies. Nat Genet 41, 843-848.

Winter, J., Jung, S., Keller, S., Gregory, R. I., and Diederichs, S. (2009). Many roads to maturity: microRNA biogenesis pathways and their regulation. Nat Cell Biol 11, 228-234.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

Zhang, W. C., Shyh-Chang, N., Yang, H., Rai, A., Umashankar, S., Ma, S., Soh, B. S., Sun, L. L., Tai, B. C., Nga, M. E., et al. (2012). Glycine decarboxylase activity drives non-small cell lung cancer tumor-initiating cells and tumorigenesis. Cell 148, 259-272.

Zhu, H., Shah, S., Shyh-Chang, N., Shinoda, G., Einhorn, W. S., Viswanathan, S. R., Takeuchi, A., Grasemann, C., Rinn, J. L., Lopez, M. F., et al. (2010). Lin28a transgenic mice manifest size and puberty phenotypes identified in human genetic association studies. Nat Genet 42, 626-630.

Zhu, H., Shyh-Chang, N., Segre, A. V., Shinoda, G., Shah, S. P., Einhorn, W. S., Takeuchi, A., Engreitz, J. M., Hagan, J. P., Kharas, M. G., et al. (2011). The Lin28/let-7 axis regulates glucose metabolism. Cell 147, 81-94.

What is claimed is:

1. An in vitro method of expanding a pool of mouse pluripotent stem cells or human pluripotent stem cells, the method comprising contacting the mouse pluripotent stem cells or the human pluripotent stem cells with at least one agent that inhibits Dis3L2 expression, in an amount effective to prevent differentiation of at least a portion of the mouse or human pluripotent stem cells, wherein the at least one agent that inhibits the expression of Dis3L2 is selected from the group consisting of an RNA interference (RNAi) molecule, a short hairpin RNA (shRNA), a short interfering RNA (siRNA) and an antisense nucleic acid; and wherein preventing differentiation of at least a portion of the mouse or human pluripotent stem cells expands the pool of mouse pluripotent stem cells or human pluripotent stem cells.

2. The method of claim 1, wherein the level of 3' uridylated pre-let-7 microRNA transcript in the pool of mouse pluripotent stem cells or human pluripotent stem cells is increased as compared to a control level of 3' uridylated pre-let-7 microRNA transcript, wherein the control level is obtained, respectively, from mouse pluripotent stem cells not exposed to the agent that inhibits Dis3L2 or human pluripotent stem cells not exposed to the agent that inhibits Dis3L2.

3. The method of claim 1, wherein the levels of expression of Sox2, Nanog and/or Oct are increased in the pool of pluripotent stem cells as compared to control expression levels of Sox2, Nanog and/or Oct, respectively, wherein the control expression levels of Sox2, Nanog and/or Oct are obtained, respectively, from mouse not exposed to the agent that inhibits Dis3L2 or human pluripotent stem cells not exposed to the agent that inhibits Dis3L2.

4. The method of claim 1, wherein the pluripotent stem cells display increased rates of proliferation as compared to a control proliferation rate, wherein the control proliferation rate is, respectively, a proliferation rate of mouse pluripotent stem cells not exposed to the agent that inhibits Dis3L2 expression or human pluripotent stem cells not exposed to the agent that inhibits Dis3L2 expression.

5. The method of claim 1, wherein the at least one agent that inhibits Dis3L2 is an agent that inhibits gene expression of Dis3L2.

6. The method of claim 5, wherein the at least one agent that inhibits gene expression of Dis3L2 is an RNA interference (RNAi) molecule.

7. The method of claim 6, wherein the RNAi molecule is a short hairpin RNA (shRNA) or a short interfering RNA (siRNA).

8. The method of claim 1, wherein the inhibitor of Dis3L2 is an antisense nucleic acid.

9. An in vitro method of expanding a pool of mouse pluripotent stem cells or human pluripotent stem cells, the method comprising contacting the mouse pluripotent stem cells or the human pluripotent stem cells with an antibody that inhibits Dis3L2 exonuclease activity, in an amount effective to prevent differentiation of at least a portion of the mouse or human pluripotent stem cells, wherein preventing differentiation of at least a portion of the mouse or human pluripotent stem cells expands the pool of mouse pluripotent stem cells or human pluripotent stem cells.

* * * * *

UNITED STATES PATENT AND TRADEMARK OFFICE
CERTIFICATE OF CORRECTION

PATENT NO. : 9,994,813 B2
APPLICATION NO. : 14/776700
DATED : June 12, 2018
INVENTOR(S) : Richard I. Gregory Page 1 of 1

It is certified that error appears in the above-identified patent and that said Letters Patent is hereby corrected as shown below:

In the Specification

At Column 1, Line 15, please replace the paragraph titled GOVERNMENT FUNDING with the following paragraph:
GOVERNMENT FUNDING
This invention was made with government support under grant number GM086386 awarded by the National Institutes of Health. The Government has certain rights in the invention.

Signed and Sealed this
Seventh Day of August, 2018

Andrei Iancu
*Director of the United States Patent and Trademark Office*

SEQUENCE LISTING

<160> NUMBER OF SEQ ID NOS: 62

<210> SEQ ID NO 1
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 1
aagcttgcgg ccgcgaacca tcctgactac aagctgaacc ttcgg       45

<210> SEQ ID NO 2
<211> LENGTH: 41

```
<212> TYPE: DNA
<213> ORGANISM: Artificial Sequence
<220> FEATURE:
<223> OTHER INFORMATION: Synthetic oligonucleotide

<400> SEQUENCE: 2
agacctagtc gactcagtcc tcaggctcct catcagacgc c                41

<210> SEQ ID NO 3
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 3
ctgctcgcga ccttaatgat gccctcgc                               28

<210> SEQ ID NO 4
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 4
gcgagggcat cattaaggtc gcgagcag                               28

<210> SEQ ID NO 5
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 5
actaggaatt cgaaccatcc tgactacaag ctgaaccttc gg               42

<210> SEQ ID NO 6
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 6
aagcttgcgg ccgctcagtc ctcaggctcc tcatcagacg cc               42

<210> SEQ ID NO 7
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 7
accatgaacc atcctgacta caagctgaac                             30

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
```
cgtcctcagg ctcctcatca g                                          21

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
aaccatcctg actacaagct gaac                                       24

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 10
tcagtcctca ggctcctcat cag                                        23

<210> SEQ ID NO 11
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 11
aacaagcggc cgcgaaccat cctgactaca agctgaacc                       39

<210> SEQ ID NO 12
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 12
aacaagaatt gagtagccca gagcagcagc                                 30

<210> SEQ ID NO 13
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 13
aacaagcggc cgcgagaaga gacctaagga aagactgtat cttcac                46

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
aacaagaatt cagtcctcag gctcctcatc                                 30

<210> SEQ ID NO 15
<211> LENGTH: 46
<212> TYPE: DNA
<213> ORGANISM: Artificial Sequence

```
<220> FEATURE:
<223> OTHER INFORMATION: Synthetic oligonucleotide

<400> SEQUENCE: 15
aacaagcggc cgcgagaaga gacctaagga aagactgtat cttcac        46

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 16
aacaagaatt gagtagccca gagcagcagc                           30

<210> SEQ ID NO 17
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 17
acggttcagc taatacgact cactataggg tgaggtagta gtttgtacag tttgagg   57

<210> SEQ ID NO 18
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 18
gcaaggcagt ggcctgtaca gttatc                              26

<210> SEQ ID NO 19
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 19
agcaaggcag tggcctgtac agttatc                             27

<210> SEQ ID NO 20
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 20
aaagcaaggc agtggcctgt acagttatc                           29

<210> SEQ ID NO 21
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 21
aaaaagcaag gcagtggcct gtacagttat c                        31
```

<210> SEQ ID NO 22
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 22
aaaaaaaaaa gcaaggcagt ggcctgtaca gttatc                                 36

<210> SEQ ID NO 23
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 23
aaaaaaaaaa aaaagcaagg cagtggcctg tacagttatc                             40

<210> SEQ ID NO 24
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 24
aaaaaaaaaa aaaaaaaaaa gcaaggcagt ggcctgtaca gttatc                      46

<210> SEQ ID NO 25
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 25
tttttttttt ttttgcaagg cagtggcctg tacagttatc                             40

<210> SEQ ID NO 26
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 26
gggggggggg ggggcaagg cagtggcctg tacagttatc                              40

<210> SEQ ID NO 27
<211> LENGTH: 73
<212> TYPE: RNA
<213> ORGANISM: Artificial Sequence
<220> FEATURE:
<223> OTHER INFORMATION: Synthetic oligonucleotide

<400> SEQUENCE: 27
ugagguagua gguuguauag uuuuaggguc acacccacca cugggagaua acuauacaau       60
cuacugucuu ucc                                                          73

<210> SEQ ID NO 28
<211> LENGTH: 87
<212> TYPE: RNA
<213> ORGANISM: Artificial Sequence

```
<220> FEATURE:
<223> OTHER INFORMATION: Synthetic oligonucleotide

<400> SEQUENCE: 28
ugagguagua gguuguauag uuuuaggguc acacccacca cugggagaua acuauacaau      60
cuacugucuu uccuuuuuuu uuuuuuu                                         87

<210> SEQ ID NO 29
<211> LENGTH: 60
<212> TYPE: RNA
<213> ORGANISM: Artificial Sequence
<220> FEATURE:
<223> OTHER INFORMATION: Synthetic oligonucleotide

<400> SEQUENCE: 29
uagcuuauca gacugauguu gacuguugaa ucucauggca acagcagucg augggcuguc      60

<210> SEQ ID NO 30
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 30
ugguuuacau gucgacuaa                                                  19

<210> SEQ ID NO 31
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 31
ugguuuacau guuguguga                                                  19

<210> SEQ ID NO 32
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 32
ggguugugau gacaggcaa                                                  19

<210> SEQ ID NO 33
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 33
gggcuaagcu gugcuauau                                                  19

<210> SEQ ID NO 34
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 34
```

-continued ccgcuuugcu gacgucaua                                                     19

<210> SEQ ID NO 35
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 35
gaauuuacgu accucucaa                                                     19

<210> SEQ ID NO 36
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 36
aggaacuacu ggacggaaa                                                     19

<210> SEQ ID NO 37
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 37
ugaaacagaa ggcguauuu                                                     19

<210> SEQ ID NO 38
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 38
gaggagaggg aagaggg                                                       17

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 39
ctttcaacat tcaccctgga tgttc                                              25

<210> SEQ ID NO 40
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 40
tgaggtagta gtttgtacag tttgagg                                            27

<210> SEQ ID NO 41
<211> LENGTH: 23
<212> TYPE: DNA
<213> ORGANISM: Artificial Sequence

```
<220> FEATURE:
<223> OTHER INFORMATION: Synthetic oligonucleotide

<400> SEQUENCE: 41
gttctctttt gcctgattcc agg                                              23

<210> SEQ ID NO 42
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 42
ctcgcttcgg cagcaca                                                     17

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 43
cagaaggaga ttactgctct ggct                                             24

<210> SEQ ID NO 44
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 44
agttgacaga catagctcgc caca                                             24

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 45
aaagcaactc agagggaacc tcct                                             24

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 46
tggtgtcttg ctctttctgt ggga                                             24

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 47
gaggaaaggg ttcttgctgg gttt                                             24
```

<210> SEQ ID NO 48
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 48
ggaaagacag tagattgtat agttatc                                              27

<210> SEQ ID NO 49
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 49
gagaccccat gaatgcagac ttt                                                  23

<210> SEQ ID NO 50
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 50
gcaaggcagt ggcctgtaca gttatc                                               26

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 51
catttggtag ctggtgcact g                                                    21

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
aacgcttcac gaatttgcgt                                                      20

<210> SEQ ID NO 53
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 53
tactcctgct tgctgatcca catc                                                 24

<210> SEQ ID NO 54
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 54
tggttggcta ggatcatgca ctca                                          24

<210> SEQ ID NO 55
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 55
tagctccttc tgcagggctt tcat                                          24

<210> SEQ ID NO 56
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 56
acactcatgt cagtgtgatg gcga                                          24

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 57
aacggtcttg ccagtacttg ctct                                          24

<210> SEQ ID NO 58
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 58
tatctcctgt accgggtggt atcatagacc ctca                               34

<210> SEQ ID NO 59
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 59
aactatacaa cctactacct ca                                            22

<210> SEQ ID NO 60
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 60
aactgtacaa actactacct ca                                            22

<210> SEQ ID NO 61
```

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 61
tgtccaagga ggatgtttca g                                              21

<210> SEQ ID NO 62
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 62
cagggatgtc agcttcataa gt                                             22
```